United States Patent [19]

Imaki et al.

[11] Patent Number: 5,403,850
[45] Date of Patent: Apr. 4, 1995

[54] DERIVATIVES OF P-SUBSTITUTED PHENYL ESTER OF PIVALIC ACID

[75] Inventors: Katsuhiro Imaki; Yoshinobu Arai; Tadao Okegawa, all of Osaka, Japan

[73] Assignee: Ono Pharmaceutical Co., Ltd., Osaka, Japan

[21] Appl. No.: 235,856

[22] Filed: Apr. 29, 1994

Related U.S. Application Data

[60] Division of Ser. No. 960,301, Oct. 13, 1992, Pat. No. 5,336,681, which is a continuation of Ser. No. 681,364, Apr. 8, 1991, abandoned, which is a division of Ser. No. 364,994, Jun. 12, 1989, Pat. No. 5,017,610.

[30] Foreign Application Priority Data

Jun. 13, 1988 [JP] Japan .................. 63-145450
Mar. 6, 1989 [JP] Japan .................. 1-53541

[51] Int. Cl.$^6$ .................. A61K 31/40; C07C 67/02
[52] U.S. Cl. .................. 514/347; 514/359; 514/546; 546/1; 548/250; 548/400; 560/250; 560/251
[58] Field of Search .................. 546/1; 548/460, 250; 560/250, 251; 514/347, 359, 546

[56] References Cited

U.S. PATENT DOCUMENTS

| | | | |
|---|---|---|---|
| 3,694,720 | 11/1954 | Denton | 560/142 |
| 3,793,292 | 2/1974 | Yamamura et al. | 260/471 |
| 4,074,059 | 2/1978 | Bullock | 560/142 |
| 4,188,390 | 2/1980 | Campbell | 424/251 |
| 4,289,865 | 9/1981 | Wilson | 560/142 |
| 4,310,682 | 1/1982 | Ozawa | 560/142 |
| 4,335,254 | 6/1982 | Wilson | 560/142 |

FOREIGN PATENT DOCUMENTS

| | | |
|---|---|---|
| 2109842 | 9/1972 | Germany . |
| 2246403 | 3/1973 | Germany . |
| 1223619 | 2/1971 | United Kingdom . |
| 2136980 | 9/1984 | United Kingdom . |

*Primary Examiner*—José G. Dees
*Assistant Examiner*—Joseph M. Conrad, III
*Attorney, Agent, or Firm*—Stevens, Davis, Miller & Mosher

[57] ABSTRACT

A derivative of general formula:

$$H_3C-\underset{\underset{CH_3}{|}}{\overset{\overset{CH_3}{|}}{C}}-\overset{O}{\overset{\|}{C}}-O-\underset{(R^3)_m}{\text{Ph}}-Y-N\overset{R^1}{\underset{R^2}{}} \quad (I)$$

wherein Y is $-SO_2-$ or $$-\overset{O}{\overset{\|}{C}}-,$$

(i) $R^1$ and $R^2$, which may the same or different, each represent, (1) $-H$,
(2) C1-16 alkyl or (3) the formula $$-X-\text{(A)}-(R^4)_n$$

wherein X is single-bond, $-SO_2-$, C1-4 alkylene, C1-4 alkylene substituted by $-COOH$ or $$-COOCH_2-\text{(Ph)}, -\text{(A)}-$$

is a pyridyl or pyrrolyl ring, n is 1~5, $R^4$ is (1) $-H$ or C1-8 alkyl, (2) C1-14 alkoxy (3) C1-6 alkylthio, (4) $-OH$, halogen, $-NO_2$ or trihalomethyl, (5) the formula: $-NR^{41}R^{42}$ wherein $R^{41}$ and $R^{42}$ each represents halogen or C1-4 alkyl, (6) tetrazole, (7) $-SO_3H$ or $-CH_2OH$, (8) the formula: $-SO_2NR^{41}R^{42}$ (9) the formula: $-Z^{41}-COOR^{43}$ wherein $Z^{41}$ is single-bond C1-4 alkylene or C2-4 alkenylene, $R^{43}$ is $-H$, C1-4 alkyl or benzyl; or non-toxic salt or an acid addition salt thereof possess inhibitory activity on elastase, and therefore is useful for treating pulmonary emphysema, atherosclerosis and rheumatoid arthritis and the like.

11 Claims, No Drawings

DERIVATIVES OF P-SUBSTITUTED PHENYL ESTER OF PIVALIC ACID

This application is a Divisional of Ser. No. 07/960,301, filed Oct. 13, 1992, now U.S. Pat. No. 5,336,681, which is a Continuation of Ser. No. 07/681,364, filed Apr. 8, 1991, now abandoned, which is a Divisional of Ser. No. 07/364,994, filed Jun. 12, 1989, now U.S. Pat. No. 5,017,610.

SUMMARY

This invention is related to the derivatives of p-substituted phenyl ester of pivalic acid having an inhibitory activity on elastase, of the general formula:

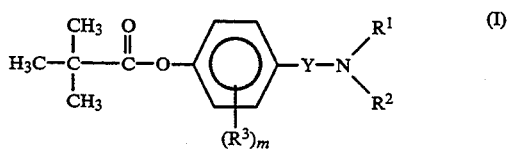

wherein $R^1$, $R^2$, $R^3$, Y and m have same meaning as described hereinafter.

BACKGROUND

Lysosomal hydrolases of neutrophils have an important role for an organism defense reaction against tissue damage caused by microbe or inflammation etc.

Elastase and cathepsin G, which belong to neutral serine proteinase locally existed in azurophil granule mainly play a part in decomposition of a connective tissue.

Especially, elastase degrades elastic connective tissue by cleaving the cross-linking of elastin which directly maintains the elasticity of lung tissue etc., and by cleaving hydrophobic part of protein [J. Cell. Biol., 40, 366 (1969)] and degrades the cross-linking area of collagen selectively as well as elastin [J. Blochem., 84, 559 (1978)], and it acts on tissue proteins such as proteoglycans etc. [J. Clin. Invest., 57, 615 (1976)]. Therefore, elastase plays an important role in metabolism of connective tissue.

Elastase is inactivated by $\alpha_1$-proteinase inhibitor ($\alpha_1$-PI) that is a common inhibitor for serine, proteinase in vivo and the unbalance of enzyme and inhibitor system causes the destruction of the tissue [Schweiz. Med. Wshr., 114, 895 (1984)].

The turnover of elastin in normal tissue is very slow [Endocrinology, 120, 92 (1978)], but the pathological acceleration in degradation of elastin is found under various unsound state such as pulmonary emphysema [Am. Rev. Respir. Dis., 110, 254 (1974)], atherosclerosis [Lab. Invest., 22, 228 (1970)] and rheumatoid arthritis [in Neutral Proteases of Human Polymorphonuclear Leukocytes, Urban and Schwarzenberg, Baltimore—Munich (1978), page 390], suggesting the relationship of elastase and diseases [Infection.Inflammation.Immunity, 13, 13 (1983)].

PRIOR ARTS

Under the background as mentioned above, recent studies and development on elastase inhibitors have been heartily conducted, and various substances inhibiting elastase have been proposed and many patent applications have been filed.

Particularly, recently, for example, in the specification of U.S. Pat. No. 4683241, the compound of the general formula:

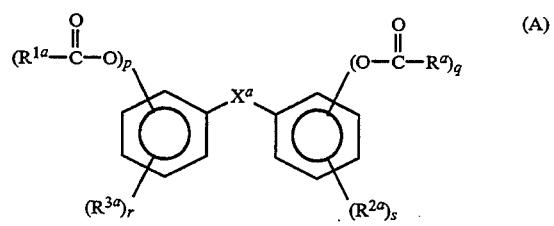

wherein $X^a$ represents a group selected from carbonyl group, methylene group, oxygen atom, azo group, sulfonyl group, —CH(OH)—,

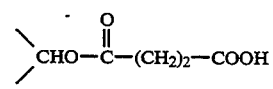

or together with the benzene rings represents the group

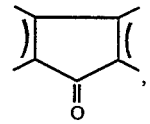

$R^a$ and $R^{1a}$ each represents an alkyl group and an acylaminoalkyl group of 2 to 6 carbon atoms, an alkoxy group, an alkenyl group and carboxyalkyl group of up to 6 carbon atoms, cycloalkyl group of 3 to 6 carbon atoms or an alkoxycarbonylalkyl group of up to 10 carbon atom(s), $R^{2a}$ and $R^{3a}$ represent hydroxy atom, halogen atom, pyranyloxy, an alkyl, an alkenyl, hydroxyalkyl and formylalkyl group of up to 4 carbon atom(s) or carboxyalkyl group of up to 6 carbon atom(s), was disclosed.

PURPOSE OF THE INVENTION

As the result of energetic investigations conducted in order to find new elastase inhibitory agents having quite different chemical structure from conventional ones, the present inventors have found that the compound of the general formula (I) achieves this purpose.

COMPARISON WITH THE PRIOR ARTS

In the specification of U.S. Pat. No. 4,683,241, benzoylphenyl ester and benzenesulfonylphenyl ester of any kind pivalic acid were disclosed as the inhibitory agent on elastase.

The structure of sulfamoylphenyl ester and carbamoylphenyl ester in the present invention can not be obvious from compounds of the Prior Art, and it have been unexpected that compounds of the present invention have inhibitory effect on elastase.

DISCLOSURE OF THE INVENTION

Accordingly, the present invention relates to the compounds of the general formula:

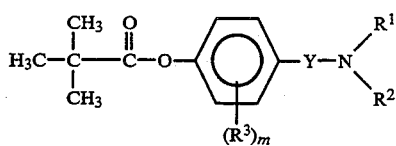 (I)

wherein Y represents sulfonyl (—SO₂—) group or carbonyl

group,
(i) R¹ and R² which may be the same or different, each represent
(1) hydrogen atom,
(2) an alkyl group of up to 16 carbon atom(s) or an alkyl group of up to 16 carbon atom(s) substituted by carboxy group
(3) a group of the formula:

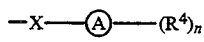

wherein X represents single-bond, sulfonyl (—SO₂) group, an alkylene group of up to 4 carbon atom(s) or an alkylene group of up to 4 carbon atom(s) substituted by —COOH group or benzyloxycarbonyl

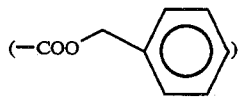

group,

represents carbocyclic ring or heterocyclic ring, n represents an integer of 1 to 5, R4 represents, same or different,
① hydrogen atom or an alkyl group of up to 8 carbon atom(s),
② an alkoxy group of up to 14 carbon atom(s),
③ an alkylthio group of up to 6 carbon atom(s),
④ hydroxy group, halogen atom, nitro group or trihalomethyl group,
⑤ a group of the formula: —NR⁴¹R⁴² wherein R⁴¹ and R⁴² each represents, same or different, hydrogen atom or alkyl group of up to 4 carbon atom(s),
⑥ tetrazole group,
⑦ sulfonic acid (—SO₃H) group or hydroxymethyl (—CH₂OH) group,
⑧ a group of the formula: —SO₂NR⁴¹R⁴² wherein R⁴¹ and R⁴² have the same meaning as described hereinbefore,
⑨ a group of the formula: —Z⁴¹—COOR⁴³ wherein Z⁴¹ represents single-bond, an alkylene group of up to 4 carbon atom(s) or an alkenylene group of from 2 to 4 carbon atoms, R⁴³ represents hydrogen atom, an alkyl group of up to 4 carbon atom(s) or benzyl group, ⑩ a group of the formula: —CONR⁴¹R⁴² wherein R⁴¹ and R⁴² have same meaning as described hereinbefore,
11 a group of the formula: —COO—Z⁴²—COOR⁴³ wherein Z⁴² represents an alkylene group of up to 4 carbon atom(s), R⁴³ represents hydrogen atom, an alkyl group of up to 4 carbon atom(s) or benzyl group,
12 a group of the formula: —COO—Z⁴²—CONR⁴¹R⁴² wherein Z⁴², R⁴¹ and R⁴² have same meaning as described hereinbefore,
13 a group of the formula: —OCO—R⁴⁵ wherein R⁴⁵ represents an alkyl group of up to 8 carbon atom(s) or p-guanidinophenyl group,
14 a group of the formula: —CO—R⁴⁶ wherein R⁴⁶ represents an alkyl group of up to 4 carbon atom(s),
15 a group of the formula: —O—Z⁴³—COOR⁴⁵⁰ wherein Z⁴³ represents an alkylene group of up to 6 carbon atom(s), R⁴⁵⁰ represents a hydrogen atom, an alkyl group of up to 8 or p-guanidinophenyl group,
16 a group of the formula:

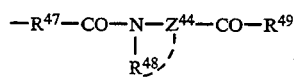

wherein

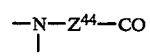

represents an amino acid residue, R⁴⁸ represents hydrogen atom or alkyl group of up to 4 carbon atom(s), and R⁴⁹ represents hydroxy group, alkoxy group of up to 4 carbon atom(s), amino group, amino group substituted by one or two alkyl group of up to 4 carbon atom(s), carbamoylmethoxy or carbamoylmethoxy group substituted by one or two alkyl group of up to 4 carbon atoms at nitrogen atom of carbamoyl group, R⁴⁷ represents single-bond or alkyl group of up to 4 carbon atom(s), or wherein

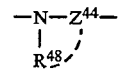

represents heterocyclic ring containing 3 to 6 carbon atoms and R⁴⁷ and R⁴⁹ has each same meaning as described hereinbefore,
(ii) R¹, R² and nitrogen atom bonded to R¹ and R² together represents heterocyclic ring containing at least one nitrogen atom(s) and substituted by —COOH, or unsubstituted heterocyclic ring containing at least one nitrogen atom(s),
R³ represents
(1) hydrogen atom,
(2) hydroxy atom,
(3) an alkyl group of up to 6 carbon atom(s),
(4) halogen atom,
(5) an alkoxy group of up to 4 carbon atom(s) or
(6) an acyloxy group of 2 to 5 carbon atoms, m represents an integer of up to 4,
or non-toxic salts or acid addition salts thereof or process for the preparation thereof, or inhibitory agents of elastase containing them as active ingredient.

In this specification and claims, the term "alkyl group", "alkylene group", "alkenylene group", "alkoxy group" and "acyloxy group" means the straight- or branched- chained alkyl group, alkylene group, alkenylene group, alkoxy group and acyloxy group.

In the general formula (I), sulfonyl and carbonyl group represented by Y are preferred.

In the general formula (I), as an alkyl group of up to 6 carbon atom(s) represented by $R^3$, methyl, ethyl, propyl, butyl, pentyl and hexyl group and the isomer thereof are cited, and all of them are preferred.

In the general formula (I), examples of the halogen atom, represented by $R^3$ and $R^4$ are, a fluorine atom, a chlorine atom, a bromine atom and an iodine.

In the general formula (I), examples of an alkoxy group of up to 4 carbon atom(s) represented by $R^3$, include methoxy, ethoxy, propoxy and butyloxy group and the isomer thereof, and all of them are preferred.

In the general formula (I), examples of an acyloxy group of 2 to 5 carbon atom(s) represented by $R^3$, include acetoxy, propionyloxy, butyryloxy and valeryloxy group and the isomer thereof are cited, and all of them are preferred.

In the general formula (I), examples of an alkyl group of up to 16 carbon atom(s) represented by $R^1$ and $R^2$, include methyl, ethyl, propyl, butyl, pentyl, hexyl, heptyl, octyl, nonyl, decyl, undecyl, dodecyl, tridecyl, tetradecyl, pentadecyl and hexadecyl group and the isomer thereof, and all of them are preferred.

In the general formula (I), examples of an alkylene group of up to 4 carbon atom(s) represented by X and $Z^{41}$, include methylene, ethylene, trimethylene and tetramethylene group and the isomer thereof, and all of them are preferred.

In the general formula (I), carbocyclic ring represented by (A) means mono- or hi-aromatic carbocyclic ring(s) containing not more than 12 carbon atoms which may be partially or fully saturated rings thereof.

Examples of these rings mentioned above are benzene, naphthalene, indene, azulene rings and partially or fully saturated rings thereof.

In the general formula (I), heterocyclic ring represented by (A) means mono-, bi-aromatic heterocyclic ring(s) containing not more than 12 carbon and hetero atoms which may be partially or fully saturated rings thereof. In above heterocyclic rings, rings containing one or two or hetero atom(s) are preferred.

Examples of these rings mentioned above are furan, thiophene, pyrrole, oxazole, isoxazole, thiazole, isothiazole, imidazole, pyrazole, furazane, pyran, pyridine, pyridazine, pyrimidine, pyrazine, indole, isoindole, benzofuran, benzothiophen, indolidine, chromen, quinoline, isoquinoline, quinolidine, purine, indazole, quinazoline, cinnoline, quinoxaline, phthalazin, pteridine rings and partially or fully saturated rings thereof.

In the general formula (I), examples of an alkyl group of up to 8 carbon atom(s) represented by $R^4$, include methyl, ethyl, propyl, butyl, pentyl, hexyl, heptyl and octyl and the isomer thereof are cited, and all of them are preferred.

In the general formula (I), examples of an alkoxy group of up to 14 carbon atom(s) represented by $R^4$, include methoxy, ethoxy, propoxy, butoxy, pentyloxy, hexyloxy, heptyloxy, octyloxy, nonyloxy, decyloxy, undecyloxy, dodecyloxy, tridecyloxy and tetradecyloxy group and the isomer thereof, and all or them are preferred, but particularly preferred are methoxy, pentyloxy, decyloxy and the isomer thereof.

In the general formula (I), examples of an alkylthio group of up to 6 carbon atom(s) represented by $R^4$, include methylthio, ethylthio, propylthio, butylthio, pentylthio and hexylthio group and the isomer thereof, and all of them are preferred.

In the general formula (I), as $R^4$, halogen, trihalomethyl, nitro, hydroxy, tetrazole, sulfonic acid and hydroxymethyl are particularly preferred.

In the general formula (I), examples of an alkyl group of up to 4 carbon atom(s) represented by $R^{41}$, $R^{42}$, $R^{43}$ and $R^{46}$, include methyl ethyl, propyl and butyl group and the isomer thereof, and all of them are preferred.

In the general Formula (I), examples of an alkenylene group of 2 to 4 carbon atom(s) represented by $Z^{41}$, include vinylene, propenylene and butenylene group and the isomer thereof, and all of them are preferred.

In the general formula (I), examples of an alkyl group of up to 8 carbon atom(s) represented by $R^{45}$ include methyl ethyl, propyl butyl, pentyl, hexyl, heptyl and octyl group and the isomer thereof, and all of them are preferred.

In the general formula (I), examples of an alkylene group of up to 6 carbon atom(s) represented by $Z^{43}$, include methylene, ethylene, trimethylene, tetramethylene, pentamethylene and hexamethylene group and the isomer thereof, and all of them are preferred.

In the general formula (I), an amino acid-residue represented by formula:

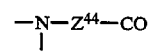

represents every amino acid-residue, and these residues contain that carboxy group was converted into ester.

Preferable amino acid-residue is neutral, acidic or basic amino acid-residue. Examples of the residues mentioned above include glycine, alanine, β-alanine, valine, phenylalanine, lysine, methionine, tyrosine, proline, leucine, tryptophan, 4-amino butyric acid, 6-aminocaproic acid, 1-amino-1-phenylacetic acid, 2-amino-2-phenylpropionic acid, m-aminobenzoic acid, p-aminobenzoic acid.

Examples of an alkyl group of up to 4 carbon atom(s) represented by $R^{48}$, include methyl, ethyl, propyl and butyl group and the isomer thereof. Included as exemplary of an alkyl, in alkoxy group represented by $R^{49}$, in substituent of amino group and in substituent of carbamoylmethoxy group, methyl, ethyl, propyl and butyl group and the isomer thereof. Exemplary of the heterocyclic ring represented by

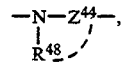

are azetidine, pyrrolidine, piperidine and perhydroazepine.

In the general formula (I), the heterocyclic ring represented by $R^1$, $R^2$ and the nitrogen atom bonded to $R^1$ and $R^2$ together, means a mono- heterocyclic ring containing 3 to 6 carbon atoms and 1 or 2 of nitrogen and/or oxygen atom(s).

Examples of these rings mentioned above are pyrrole, imidazole, pyrazole, pyrroline, pyrrolidine, imidazoline, imidazolidine, pyrazoline, pyrazolidine, piperidine, piperazine, morpholine, azetidine.

An acid addition salts of the compound of the general formula (I) are preferred non-toxic and water-soluble salts.

Suitable acid addition salts include, for example, an inorganic acid addition salt such as hydrochloride, hydrobromide, hydroiodide, sulfate, phosphate, nitrate, or an organic acid addition salt such as acetate, lactate, tartrate, benzoate, citrate, methanesulfonate, ethanesulfonate, benzenesulfonate, toluenesulfonate, isethionate, glucuronate, gluconate.

The compounds of the present invention of the general formula (I) may be converted into the corresponding salts by known methods. Non-toxic and water-soluble salts are preferable. Suitable salts, for example, are as follows: salts of alkaline metal (sodium, potassium etc.), salts of alkaline earth metal (carcium, magnesium etc.), ammonium salts, salts of pharmaceutically acceptable organic amine (tetramethylammonium, triethylamine, methylamine, dimethylamine, cyclopentylamine, benzylamine, phenethylamine, piperidineamine, monoethanolamine, diethanolamine, tris (hydroxymethyl)amine, lysine, arginine, N-methyl-D-glucamine etc.)

PROCESS FOR THE PREPARATION

According to the present invention, the compounds of the present invention of the general formula (I) may be prepared by any step described hereinafter.

In each formula, $R^{11}$ and $R^{21}$ have same meaning as that of $R^1$ and $R^2$, respectively provided that at least either $R^{11}$ or $R^{21}$ represents benzyloxycarbonyl group, $R^{12}$ and $R^{22}$ have same meaning as that of $R^1$ and $R^2$, respectively provided that at least either $R^{12}$ or $R^{22}$ represents carboxyl group, $R^{13}$ has same meaning that of $R^1$ or $R^2$ other than hydrogen atom, $R^{14}$ represents an alkyl group of up to 4 carbon atom(s), X represents halogen atom, $R^{31}$ represents an acyloxy group.

Step 1:

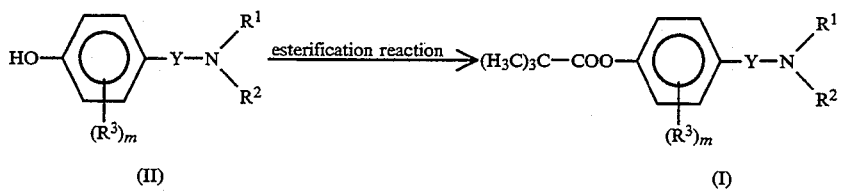

Step 2:

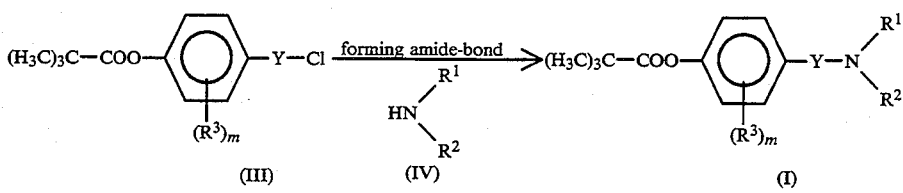

Step 3:

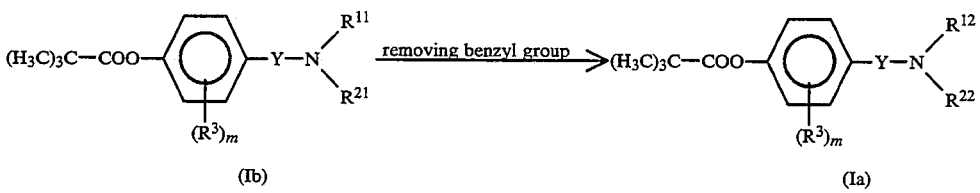

Step 4:

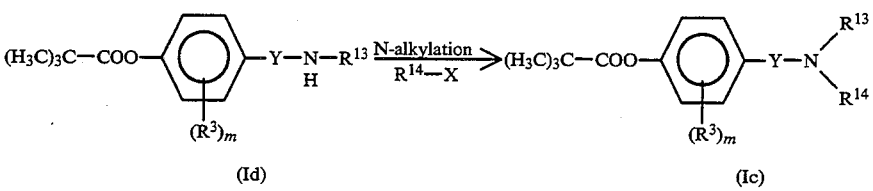

Step 5:

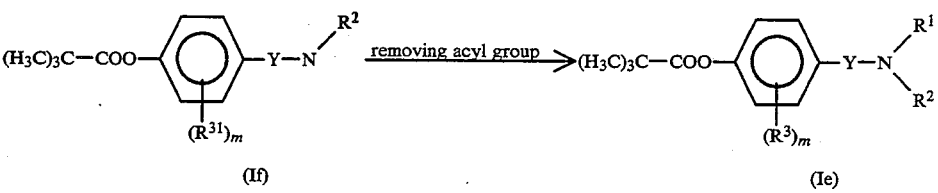

Step 1, which is an esterification reaction, conducted in the presence of a dehydrohalogenation agent in inert organic solvents (for example, methylene chloride, ethyl acetate, benzene, hexane, diethylether), may be carried out by reacting with corresponding pivaloyl halide under room temperature.

As for the dehydrohalogenation agent, there can be used a tertiary organic amine, or if desired, there can be used a inorganic base such as a metal bicarbonate, etc.

As a tertiary organic amine, there can be used aliphatic, aromatic or heterocyclic amine, for example, triethylamine, tributylamine, dimethylaniline, pyridine and the like.

Particularly, pyridine is preferable because it is useful also as a solvent of reaction ingredient.

Step 2, which is reaction forming the amide-bond, may be carried out by reacting the compound of the general formula (III) with corresponding amine in inert organic solvent (for example methylene chloride), in the presence of organic or inorganic base (for example, tertiary amine such as triethylamine), at a temperature of $-20°$ C.$\sim 0°$ C. (preferably under cooling with ice).

Step 3, which is reaction for removing a benzyl group, may be carried out under an atmosphere of hydrogen gas, using palladium-carbon as catalyst in a mixture of inert organic solvent (for example acetic acid, THF), at a temperature of 0° C. to 40° C.

Step 4, which is N-alkylation reaction, may be carried out reacting with alkyl halide in suitable inert organic solvent (for example, benzene, tetrahydrofuran, dimethylformamide), in the presence of a suitable base (for example, sodium hydride), at from about room temeprature to reflux temperature.

Step 5, which is reaction for eliminating the acyl group, may be carried out for example, in methanol, in the precense of a catalyst (for example, triethylamine), at or about room temperature.

The compounds of the general formula (II) and (III) used in the step hereinbefore may be prepared by combining known methods, for example according to scheme A hereinafter.

In the formula, G represents methoxy group or acetoxy group, and the other symbols have same meaning as described hereinbefore.

Scheme A

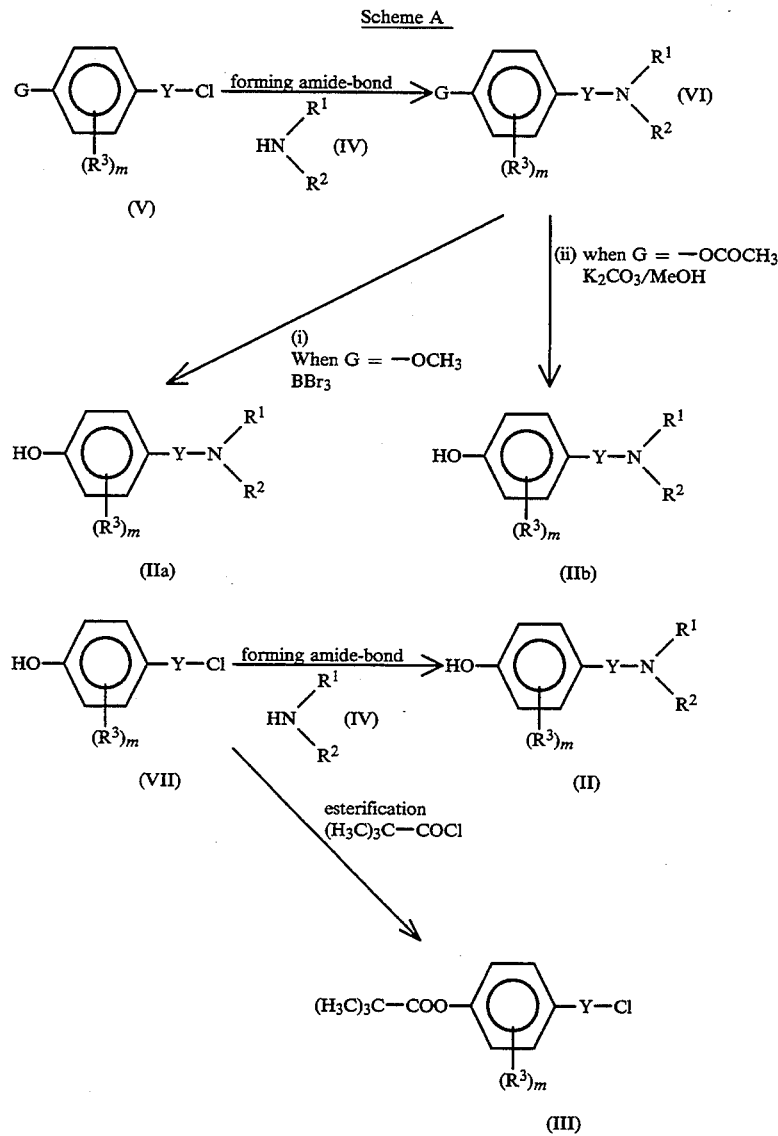

All reactions in the above schemes may be carried out by known methods.

In each reaction in the present specification, products may be purified by conventional manner. For example, purification may be carried out by distillation at atomospheric or reduced pressure, high performance liquid chromatography, thin layer chromatography or column chromatography using silica gel or magnesium silicate, washing or recrystallization. Purification may be carried out after each reaction, or after a series of reactions.

STARTING MATERIALS

The starting materials of formula (IV), (V) and (VII) in Scheme A are known compounds, or may be easily prepared by known methods.

For example, when $R^1$ and $R^2$ in the formula (IV) each represents $R^1$ and (3)- 16 of $R^2$ in the formula (I) mentioned above, those may be prepared according to scheme B described hereinafter.

In the formula, the sum of p and r represents an integer of 1 to 5, and r does not represent zero. $R^{24}$ has same meaning that of $R^4$ other than (3) - 16.

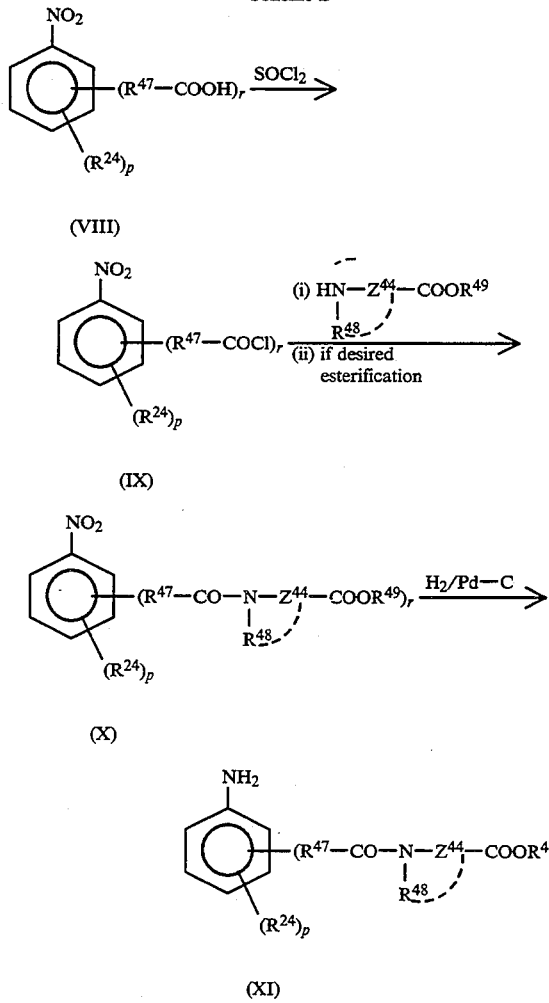

EFFECT

Derivatives of p-substituted phenyl ester of pivalic acid of the general formula (I) of the present invention, and non-toxic acid and acid addition salts thereof, have an inhibitory effect on elastase.

Accordingly, the derivatives of the present invention are useful for treatment and/or prevention of diseases induced by the abnormal enhancing of the degradation of elastin, collagen fiber and/or proteoglican, by the action of elastase, in mammals, especially in human beings.

Examples of such diseases are pulmonary emphysema, atherosclerosis, rheumatoid arthritis and the like.

The inhibitory effects of the compounds of the invention on elastase were confirmed by the screening system desclosed below.

INHIBITORY EFFECT ON ELASTASE (1) Method of Experiment

The test was carried out by a slight modification of the method of Bieth et al [see Biochem. Med., 75, 350 (1974) ] using elastase from human neutrophil.

Namely, it is a spectrophotometric method using the synthesized substrate [succinyl-alanyl-prolyl-alanyl-p-nitroanilide (Suc-Ala-Pro-Ala-pNA, produced by peptide laboratory)] which has comparatively high specificity on neutrophil elastase.

The reaction mixture consisted of 1 mM Suc-Ala-Pro-Ala-pNA (dissolving in N-methylpyrrolidone to the concentration of 100 mM, and then adding 1/100 amount of the solution to the reaction mixture.), 0.1 M buffer solution of tris-hydrochloric acid (pH 8.0), 0.2 M sodium chloride aqueous solution, the sample solution of various concentrations and enzyme solution in a final volume of 1.0 ml was incubated at 37° C. for 30 minutes.

The reaction was stopped by the addition of 100 μl of 50% acetic acid into the reaction mixture, and then p-nitro anilide released was measured on absorbance of 405 nm.

Inhibition percentage of the test compounds was calculated by the following equation:

Inhibition (%) =

$$\left(1 - \frac{OD_{405} \text{ nm count of sample} - \text{background}}{OD_{405} \text{ nm count of control} - \text{background}}\right) \times 100$$

(2) Results

The results are shown in Table 1.

TABLE I

Inhibitory effect of elastase

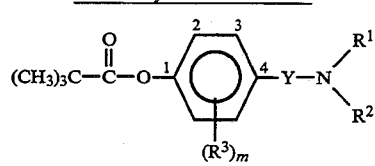

| Example No. | Structure | Name | Inhibitory effect of elastase (μM) |
|---|---|---|---|

TABLE I-continued

Inhibitory effect of elastase

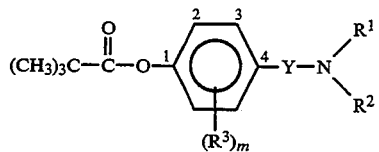

| # | Structure | Name | Value |
|---|---|---|---|
| 1 | Ph-SO₂N(CH₃)-C₆H₄-Br | p-[N-(p-bromophenyl)-N-methylsulfamoyl] phenyl ester of pivalic acid | 0.031 |
| 1(2) | Ph-SO₂NH₂ | p-sulfamoylphenyl ester of pivalic acid | 0.77 |
| 1(3) | Ph-SO₂NH-cyclohexyl | p-(N-cyclohexylsulfamoyl)phenyl ester of pivalic acid | 0.042 |
| 1(8) | Ph-SO₂NH-C₆H₄-Cl | p-[N-(p-chlorophenyl)sulfamoyl]phenyl ester of pivalic acid | 0.03 |
| 1(12) | Ph-SO₂N-imidazolyl | p-[(1-imidazolyl)sulfonyl]phenyl ester of pivalic acid | 0.05 |
| 1(14) | Ph-SO₂NH-(2-pyridyl) | p-[N-(α-pyridyl)sulfamoyl]phenyl ester of pivalic acid | 0.19 |
| 1(15) | Ph-SO₂N(C₆H₄-OCCH₃)(SO₂-C₆H₄-OCC(CH₃)₃) | 1-acetoxy-4-[N,N-bis(p-pivaloyloxy-phenylsulfonyl)amino]benzene | 0.048 |
| 2(5) | Ph-SO₂NH-C(CH₃)₃ | p-(N-tert-butylsulfamoyl)phenyl ester of pivalic acid | 0.053 |
| 2(38) | CH₃-Ph-SO₂NH-C₆H₄(COOCH₂CON(C₂H₅)₂) | 2-methyl-4-[N-(o-(N,N-diethylcarbamoylmethoxycarbonyl)phenyl)sulfamoyl]phenyl ester of pivalic acid | 0.072 |

TABLE I-continued

Inhibitory effect of elastase

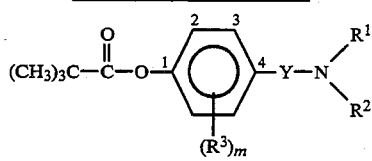

| Example No. | Structure | Name | Inhibitory effect of elastase (μM) |
|---|---|---|---|
| 2(49) | CH₃—C₆H₃(SO₂NH)—C₆H₄ fused with 1,4-dioxane bearing COOH | 2-methyl-4-[N-(1,4-dioxa-2-carboxy-8-yl-naphthalene)sulfamoyl]phenyl ester of pivalic acid | 0.15 |
| 2(51) | CH₃—C₆H₃(SO₂NH)—C₆H₄—O—(CH₂)₃—COOH | 2-methyl-4-[N-(o-carboxypropoxyphenyl)sulfamoyl]phenyl ester of pivalic acid | 0.64 |
| 2(62) | CH₃—C₆H₃(SO₂NH)—C₆H₄—CON(prolyl)COOH | 2-methyl-4-[N-(o-prolylcarbonylphenyl)sulfamoyl]phenyl ester of pivalic acid | 0.69 |
| 2(63) | C₆H₄(SO₂NH)—C₆H₄—CONHCH₂COOH | N-[O-(p-pivaloyloxybenzene)sulfonylaminobenzoyl]glycine | 0.044 |

| Example No. | Structure (R3)m | Name | Inhibitory effect of elastase (μM) |
|---|---|---|---|
| 2(67) | CH₃—C₆H₃(SO₂NH)—C₆H₄—CONH—CH(CH₂C₆H₅)—COOH | N-[O-(3-methyl-4-pivaloyloxybenzene)sulfonylaminobenzoyl]-L-phenylanine | 0.41 |
| 2(68) | CH₃—C₆H₃(SO₂NH)—C₆H₄—CONH—CH((CH₂)₂SCH₃)—COOH | N-[O-(3-methyl-4-pivaloyloxybenzene)sulfonylaminobenzoyl]-dl-methionine | 0.20 |
| 2(69) | CH₃—C₆H₃(SO₂NH)—C₆H₄—CONH—CH((CH₂)₄NH₂)—COOH·HCl | N-[O-(3-methyl-4-pivaloyloxybenzene)sulfonylaminobenzoyl]-L-lysine hydrochloride | 0.52 |

TABLE I-continued

Inhibitory effect of elastase

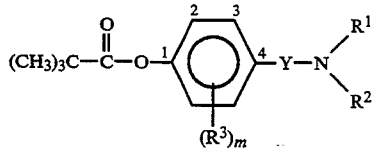

| | | | |
|---|---|---|---|
| 2(80) | [structure: phenyl-SO2NH-phenyl with CONHCH2COOH and SCH3] | N-[5-methylthio-2-(p-pivaloyloxybenzene)sulfonylaminobenzoyl]glycine | 0.021 |
| 2(87) | [structure: phenyl-SO2NH-phenyl with CONHCH2COOH and S(CH2)2CH3] | N-[2-(p-pivaloyloxybenzene)sulfonylamino-5-propylthiobenzoyl]glycine | 0.024 |
| 4(5) | [structure: phenyl-SO2NH-(CH2)2-phenyl] | p-(N-phenetylsulfamoyl)phenyl ester of pivalic acid | 0.072 |
| 5(3) | [structure: phenyl-SO2NH-phenyl-COOH] | p-[N-(o-carboxyphenyl)sulfamoyl]phenyl ester of pivalic acid | 0.023 |

The result of tile experiment showed that the compounds of the present invention have an inhibitory effect on elastase.

TOXICITY

Further, it was confirmed that the toxicity of the compounds of the present invention is low enough such that they can be used safely for medical supplies.

APPLICATION

Accordingly, it was confirmed that the compounds of the present invention can be useful for the treatment and/or prevention of diseases induced by abnormal enhancing of degradation of proteins such as elastin and the like, by the action of elastase in mammals, especially in human beings.

ADMINISTRATION

For the purpose mentioned above, the compounds of the present invention, described in the general formula (I) or an acid addition salts thereof may normally be administered systemically or partially, usually by oral or parenteral administration.

The dose to be administered is determined depending upon age, body weight, symptom, the desired therapeutic effect, the route of administration, and the duration of the treatment etc. In the human adult, the doses per person for one time are generally between 1 mg and 500 mg, by oral administration up to several times per day, and between 0.1 mg and 200 mg, by parenteral administration (preferably by intravenous administration) up to several times per day.

As mentioned above, the doses to be used depend on various conditions. Therefore, there are cases in which doses lower than the ranges specified above and doses greater than tile ranges specified above, may be used.

Solid compositions according to the present invention for oral administration include compressed tablets, dispersible powders and granules. In such solid compositions, one or more of tile active compound(s) is, or are, admixed with at least one inert diluent such as lactose, mannitol, glucose, hydroxypropyl cellulose, microcrystalline cellulose, starch, polyvinyl-pyrrolidone or magnesium metasilicate aluminate. The compositions may also comprise, as is normal practice, additional substances other than inert diluents e.g. lubricating agents such as magnesium stearate, and, disintegrating agents such as cellulose calcium glycolate, stabilizing agents such as lactose, and solubilizers such as glutamic acid and asparaginic acid. The tablets or pills may, if desired, be made into gastric film-coated or enteric film-coated tablets or pills, such as sugar-coated, gelatin-coated, hydroxypropylcellulose-coated or hydroxypropylmethylcellulose phthalate-coated tablets or pills; two or more layers may be used. The compositions For oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s). Besides inert diluents such compositions may also comprise stabilizers such as sodium bisulfite and buffer for isotonicity, for example sodium chloride, sodium citrate or citric acid.

The manufacturing methods of spray compositions have been described in detail, for example, in the specifications of U.S. Pat. No. 2,868,691 and U.S. Pat. No. 3,095,355.

Preparations for injection according to the present invention for parenteral administration include sterile aqueous or non-aqueous solutions, suspensions or emulsions. Example of aqueous solvents or suspending media are distilled water for injection and physiological salt solution. Examples of non-aqueous solvents or suspending media are propylene glycol, polyethylene glycol, vegetable oils such as olive oil, alcohols such as ehtanol, Polysorbate 80 (registered Trade Mark). These compositions may also include adjuvants such as preserving, wetting, emulsifying and dispersing agents stabilizing agents (e.g. lactose) and solubilizers (e.g. glutamic acid and asparaginic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries for vaginal administration which comprise one or more of the active compound(s) and may be prepared by known methods.

EXAMPLES AND COMPARATIVE EXAMPLES

The following Reference Examples and Examples illustrate the preparation of compounds of the present invention, however, the present invention is not restricted to them. In the Reference Examples and Examples, "TLC", "NMR" and "IR" each represents "thin layer chromatography", "nuclear magnetic resonance" and "infrared absorption spectrum", respectively.

The solvents in the parentheses show the developing or eluting solvents and the ratios of the solvents used are by volume in chromatographic separation. Unless otherwise specified, "IR" were measured by KBr method, and "NMR" were measured in bichloroform (CDCl₃).

Reference Example 1

1-(N-methyl-N-phenyl)sulfamoyl-4-methoxybenzene

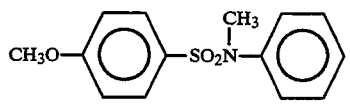

p-methoxybenzenesulfonyl chloride (965 mg) was dissolved in the mixture of triethylamine (2 ml), methylaniline (500 mg) and methylene chloride (10 ml) under cooling with ice, and the mixture was stirred for 30 minutes.

The reaction solution was stirred overnight at room temperature. After the reaction was finished, the reaction solution was extracted with ether. The extract was washed successively with 1N-HCl, water and a saturated aqueous solution of sodium chloride.

The solution was dried over sodium sulfate, and distilled off under reduced pressure to give the title compounds.

Reference Example 2 p-[N-methyl-N-(p-bromophenyl)sulfamoyl]phenol

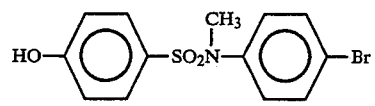

Boron tribromide (2.2 ml) was added to the solution of methylene chloride (10 ml) of the compound obtained by Reference Example 1 under cooling with ice, and stirred for 2 hours at room temperature.

The reaction solution was allowed to cool to −20° C.~−30° C., and water was added thereto, and the solution obtained was extracted with ethyl acetate. The extract was washed successively with water and saturated aqueous solution of sodium chloride.

The solution was dried over sodium sulfate, and distilled off under reduced pressure and tile residue was purified by column chromatography on silica-gel (methylene chloride:ehtyl acetate=10:1) to give the title compound (900 mg) having the following physical data:

TLC:Rf 0.20 (methylene chloride:ethyl acetate=30:1).

Reference Example 3 p-[N-[(p-tolyl)carbamoyl]phenol

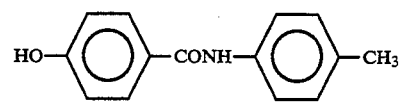

Potassium carbonate (500 mg) was added into methanol solution (50 ml) of [p-acetoxy-N-(p-tolyl)]benzamide {300 mg) obtained by the same procedure as Reference Example 1, and the mixture was stirred overnight.

The obtained reaction solution was distilled off under reduced pressure, and extracted with ethyl acetate. The extract was washed successively with 1N-hydroic acid, water and saturated aqueous solution of sodium chloride.

The solution was dried with magnesium sulfate, and distilled off under reduced pressure to give the title compound having the following physical data.

TLC:Rf 0.31 (methylene chloride:ethyl acetate:=10:1).

Example 1 p-[N-(p-bromophenyl)-N-methylsulfamoyl]phenyl ester of pivalic acid

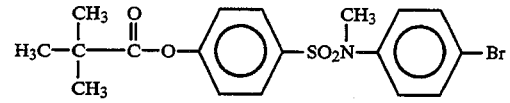

Pivaloyl chloride (0.5 ml) was added to the mixture solution of triethylamine (1.5 ml)-methylene chloride (5 ml) of the compounds obtained by procedure of Reference Example 2 under cooling with ice. The reaction solution was allowed to stand for 10 minutes, and stirred for one hour at room temperature.

The reaction solution was extracted with ether, and the extract was washed successively with water, 1N-HCl, water, saturated aqueous solution of sodium bicarbonate, water and saturated aqueous solution of sodium chloride. The solution was dried with sodium sulfate, and distilled off under reduced pressure.

The concentrate was recrystallized with ethyl acetate-hexane to give the title compound (510 mg) having the following physical data.

TLC:Rf 0.81 (methylene chloride:ethyl acetate=30:1);

IR:1750, 1590, 1460, 1400, 1350 cm$^{-1}$.

Hereinafter, the title compound, which was described in the following Table II and III, was given by using corresponding starting materials and by operating the same procedure as Reference Example 1→Reference Example 2 (or Reference Example 3)→Example 1.

TABLE II

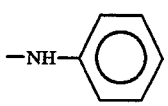

| Example No. | $-N\begin{smallmatrix}R^1\\R^2\end{smallmatrix}$ | Name | TLC | IR (cm$^{-1}$) or NMR |
|---|---|---|---|---|
| 1(1) | 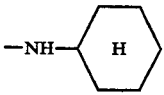 | p-(N-phenylsulfamoyl)phenyl ester of pivalic acid | Rf 0.3 (hexane: ethyl acetate: = 5:2) | δ 7.7(2H, d), 7.3~6.9(7H, m), 6.5(1H, 6s), 1.3(9H, s) |
| 1(2) | —NH$_2$ | p-sulfamoylphenyl ester of pivalic acid | Rf 0.72 (hexane: ethyl acetate: = 1:2) | υ 3400, 3280, 1720, 1580, 1480, 1350, 1200, 1160, 1120 |
| 1(3) | 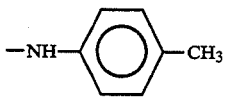 | p-(N-cyclohexylsulfamoyl)phenyl ester of pivalic acid | Rf 0.82 (hexane: ethyl acetate: = 1:1) | υ 3280, 2940, 1750, 1590, 1480, 1440, 1320, 1210, 1160, 1100 |
| 1(4) | 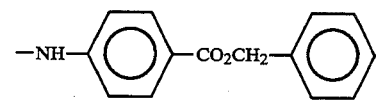 | p-[N-(p-tolyl)sulfamoyl]phenyl ester of pivalic acid | Rf 0.62 (methylene chloride: ethyl acetate: = 30:1) | υ 3300, 1740, 1580, 1500, 1380, 1330, 1270, 1200 |
| 1(5) | 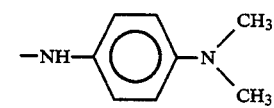 | p-[N-(p-benzyloxycarbonyl-phenyl)sulfamoyl]phenyl ester of pivalic acid | Rf 0.75 (hexane: ethyl acetate: = 1:1) | υ 1750, 1720, 1600, 1460, 1340, 1270, 1150, 1100 |
| 1(6) | 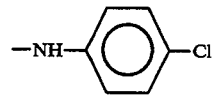 | p-[N-(4-N,N-dimethyl-amino)phenyl)sulfamoyl]phenyl ester of pivalic acid | Rf 0.78 (hexane: ethyl acetate: = 1:2) | υ 1750, 1610, 1590, 1520, 1330, 1200, 1150, 1100 |
| 1(7) | —NH—C$_{10}$H$_{21}$ | p-(N-decylsulfamoyl)phenyl ester of pivalic acid | Rf 0.6 (methylene chloride: ethyl acetate: = 30:1) | υ 3300, 2930, 2850 1750, 1590 |
| 1(8) | 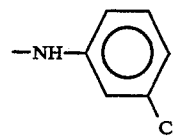 | p-[N-(4-chlorophenyl)sulfamoyl] phenyl ester of pivalic acid | Rf 0.52 (methylene chloride: ethyl acetate: = 30:1) | υ 3260, 2970, 1750, 1590, 1490, 1450, 1340 |
| 1(9) |  | p-[N-(m-chlorophenyl)sulfamoyl] phenyl ester of pivalic acid | Rf 0.50 (methylene chloride: ethyl acetate: = 30:1) | υ 3250, 1750, 1590, 1480, 1400, 1330, 1200 |

TABLE II-continued $$(CH_3)_3C-\overset{O}{\underset{\|}{C}}-O-\underset{(R^3)_m}{\overset{}{\bigcirc}}-SO_2N\overset{R^1}{\underset{R^2}{}}$$

| Example No. | $-N\overset{R^1}{\underset{R^2}{}}$ | Name | TLC | IR (cm$^{-1}$) or NMR |
|---|---|---|---|---|
| 1(10) | -NH-⟨pyridyl-β⟩ | p-[N-(β-pyridyl)sulfamoyl]phenyl ester of pivalic acid | Rf 0.50 (methylene chloride: methanol = (10:1) | υ 3600~3200, 1750, 1580, 1470, 1400, 1350, 1310, 1260, 1200 |
| 1(11) | -NH-⟨C$_5$H$_{11}$⟩ | p-[N-(p-pentylphenyl)sulfamoy]phenyl ester of pivalic acid | Rf 0.46 (methylene chloride: ethyl acetate: = 30:1) | υ 3960, 3920, 3850, 3250, 1750, 1610, 1590, 1510, 1480, 1460, 1400, 1330 (neat) |
| 1(12) | -N⟨imidazolyl⟩ | p-[(1-imidazolyl)sulfonyl]phenyl ester of pivalic acid | Rf 0.52 (methylene chloride: ethyl acetate: = 5:1) | δ 7.96(2H, d), 8.0 (1H, m), 7.28(2H, d), 7.28(1H, m), 7.09(1H, m), 1.36 (9H, s) |
| 1(13) | -N⟨morpholino⟩O | (p-morpholinosulfonyl)phenyl ester of pivalic acid | Rf 0.19 (methylene chloride: ethyl acetate: = 30:1) | υ 2970, 2860, 1759, 1590, 1480, 1340 |
| 1(14) | -NH-⟨pyridyl-α⟩ | p-[N-(α-pyridyl)sulfamoyl]phenyl ester of pivalic acid | Rf 0.64 (chloroform: methanol: = 30:1) | υ 3200~2300, 1750, 1630, 1610, 1520, 1490, 1480, 1460, 1380, 1360 |
| 1(15) | -N(bis-aryl structure with OCCH$_3$ and SO$_2$-⟨⟩-O-C(=O)-C(CH$_3$)$_3$) | 1-methoxy-4-[N,N-bis(p-pivaloyloxyphenylsulfonyl) amino]benzene | Rf 0.61 (methylene chloride: ethyl acetate = 30:1) | υ 3400, 2970, 1750, 1590, 1480 |

TABLE III $$(CH_3)_3C-\overset{O}{\underset{\|}{C}}-O-\underset{(R^3)_m}{\overset{}{\bigcirc}}-CON\overset{R^1}{\underset{R^2}{}}$$

| Example No. | $-N\overset{R^1}{\underset{R^2}{}}$ | Name | TLC | IR (cm$^{-1}$) or NMR |
|---|---|---|---|---|
| 1(16) | -NH-⟨CH$_3$⟩ | p-[N-(p-tolyl)carbamoyl]phenyl ester of pivalic acid | Rf 0.46 (methylene chloride: ethyl chloride: = 30:1) | υ 3300, 2960, 1740, 1640, 1600, 1500 |

Reference Example 4 sodium salt of p-pivaloyloxybenzenesulfonic acid

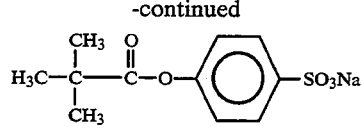

Pivaloyl chloride (2.4 g) was dissolved in the mixture of 4N-aqueous solution of sodium hydroxide (7.5 ml) of phenol 4-sulfonic acid (1.74 g) and tetrahydrofuran (5 ml), and the mixture was stirred for 10 minutes under cooling with ice. The mixture was reacted for one hour at room temperature.

The reaction solution was distilled off under reduced pressure, and tile crystal was filtered off.

The obtained crystal was washed twice with a small amount of ice-water, and dried to give the title compound (1.26 g) having the following physical data.

TLC:Rf 0.65 (ethyl acetate:acetic acid:water=6:2:1).

Reference Example 5 p-pivaloyloxybenzenesulfonyl chloride

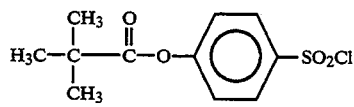

Thionyl chloride (2.1 ml) was added to dimethylformamide solution (33 ml) of the compound (2.8 g) of Reference Example 4, and the mixture was stirred for 30 minutes under cooling with ice, and stirred for 30 minutes at room temperature.

The reaction solution was extracted with ether-hexane (1:1), and the extract was washed twice with ice-water.

The solution was dried with magnesium sulfate to give the title compound (2.49 g) having the following physical data.

TLC:Rf 0.34 (hexane:ethyl acetate=10:1).

Example 2 p-[N-((trans-p-carboxycyclohexyl)methyl)sulfamoyl[phenyl ester of pivalic acid

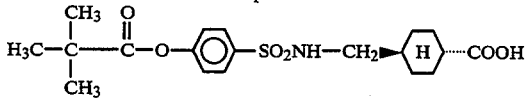

By using sulfonyl chloride of Reference Example 5, and by the same procedure of Reference Example 1, the title compound (110 mg) having the following physical data was obtained.

TLC:Rf 0.32 (chloroform:methanol:acetic acid=100:5:1)

NMR:7.9(2H,d), 7.25(2H,d), 4.4(1H,m), 2.8(2H,m), 2.4~1.0(9H,m), 1.35(9H,s).

Hereinafter, by using sulfonyl chloride of Reference Example 5 and corresponding amine, and by the same procedure of Example 2, the desired compounds described in tile following Table IV and V were obtained.

TABLE IV

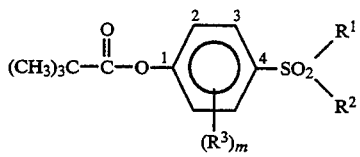

| Example No. | $-N\begin{matrix}R^1\\R^2\end{matrix}$ $-R^{3*}$ | Name | TLC | IR (cm$^{-1}$) or NMR |
|---|---|---|---|---|
| 2(1) | —NH—⟨phenyl⟩—CH$_2$COOH<br>—H | p-[N-(p-carboxymethylphenyl)sulfamoyl]phenyl ester of pivalic acid | Rf 0.3 (chloroform: methanol: acetic acid = 100:5:1) | (CDCl$_3$ + CO$_3$OD): δ 7.8(2H, d), 7.4~7.0(6H, m), 3.55(2H, s), 1.35(9H, s) |
| 2(2) | —NH—⟨phenyl⟩—CH=CH—COOH<br>—H | p-[N-(p-(trans-2-carboxyvinyl)phenyl)sulfamoyl]phenyl ester of pivalic acid | Rf 0.33 (chloroform: methanol: acetic acid = 100:5:1) | (CDCl$_3$ + CD$_3$OD): δ 8.0~7.0(10H, m), 6.2(1H, d), 1.35(9H, s) |
| 2(3) | —NH—⟨phenyl-COOH⟩<br>—H | p-[N-(m-carboxyphenyl)sulfamoyl]phenyl ester of pivalic acid | Rf 0.31 (chloroform: methanol: acetic acid = 100:5:1) | (CDCl$_3$ + CO$_3$OD): δ 8.0~7.0(10H, m), 6.2(1H, d), 1.35(9H, s) |
| 2(4) | —NH—CH$_2$—⟨phenyl⟩—COOH<br>—H | p-[N-(p-carboxybenzyl)sulfamoyl]phenyl ester of pivalic acid | Rf 0.31 (chloroform: methanol: acetic acid = 100:5:1) | δ 8.1~7.8(4H, m), 7.5~7.2(5H, m), 4.2(2H, s), 1.35(9H, s) |
| 2(5) | —NH—C(CH$_3$)$_3$<br>—H | p-(N-tert-butylsulfamoyl)phenyl ester of pivalic acid | Rf 0.65 (methylene chloride: | ν 3260, 2980, 1740, 1590, 1480, 1310, 1200 |

TABLE IV-continued

Structure: (CH₃)₃C-C(=O)-O-[phenyl with positions 1,2,3,4, (R³)ₘ]-SO₂-NR¹R²

| Example No. | -R³*, -NR¹R² | Name | TLC | IR (cm⁻¹) or NMR |
|---|---|---|---|---|
| | | | ethyl acetate = 30:1 | |
| 2(6) | -NH-(C₆H₄)-O-C(=O)-CH₃; -H | p-[N-(p-acetoxyphenyl)sulfamoyl] phenyl ester of pivalic acid | Rf 0.58 (ethyl acetate: hexane = 1:1) | ν 3260, 2960, 1750, 1740, 1590, 1300, 1470, 1400, 1340, 1230, 1190, 1150, 1100 |
| 2(7) | -NH-(C₆H₄)-OH; -H | p-[N-(p-hydroxyphenyl)sulfamoyl] phenyl ester of pivalic acid | Rf 0.08 (methylene chloride: ethyl acetate = 30:1) | ν 1745, 1590, 1510, 1400, 1320, 1270, 1200 |
| 2(8) | -NH-(C₆H₄)-OH (meta); -H | p-[N-(m-hydroxyphenyl)sulfamoyl] phenyl ester of pivalic acid | Rf 0.10 (methylene chloride: ethyl acetate = 30:1) | ν 3400, 3240, 1640, 1610, 1600, 1480 |
| 2(9) | -NH-(4-pyridyl); -H | p-[N-(4-pyridyl)sulfamoyl]phenyl ester of pivalic acid | Rf 0.30 (chloroform: methanol = 10:1) | ν 3500~2300, 1750, 1630, 1590, 1490, 1350 |
| 2(10) | -NH-(C₆H₄)-SO₂NH₂; -H | p-[N-(p-sulfamoylphenyl)sulfamoyl] phenyl ester of pivalic acid | Rf 0.18 (chloroform: methanol: acetic acid = 100:5:1) | (CDCl₃ + CD₃OD): ν 7.9(2H, d), 7.75 (2H, d), 7.3(2H, d), 7.2(2H, d), 1.35(9H, s) |
| 2(11) | -NH-(C₆H₄)-CONH₂; -H | p-[N-(p-carbamoylphenyl)sulfamoyl] phenyl ester of pivalic acid | Rf 0.22 (chloroform: methanol: acetic acid = 100:5:1) | (CDCl₃ + CD₃OD): ν 7.85(2H, d), 7.70(2H, d), 7.18(2H, d), 7.14(2H, d) |
| 2(12) | -NH-CH₂-(α-pyridyl); -H | p-[N-(α-pyridylmethyl)sulfamoyl] phenyl ester of pivalic acid | Rf 0.75 (chloroform: methanol: = 10:1) | ν 1750, 1590, 1480, 1330, 1200, 1160 |
| 2(13) | -NH-CH₂-(β-pyridyl); -H | p-[N-(β-pyridylmethyl)sulfamoyl] phenyl ester of pivalic acid | Rf 0.57 (chloroform: methanol: = 10:1) | ν 1750, 1590, 1480, 1320, 1200, 1150, 1100 |
| 2(14) | -NH-CH₂-(4-pyridyl); -H | p-[N-(4-pyridylmethyl)sulfamoyl] phenyl ester of pivalic acid | Rf 0.57 (chloroform: methanol: = 10:1) | ν 1750, 1600, 1590, 1480, 1420, 1320, 1200 |

TABLE IV-continued

Structure:
$(CH_3)_3C-C(=O)-O^{-1}-[phenyl\ ring\ with\ positions\ 2,3,4]-SO_2-NR^1R^2$, with $(R^3)_m$ substituent on ring.

| Example No. | $-N(R^1)(R^2)$ / $-R^{3*}$ | Name | TLC | IR (cm$^{-1}$) or NMR |
|---|---|---|---|---|
| 2(15) | $-NH-$(o-hydroxyphenyl); $-H$ | p-[N-(o-hydroxyphenyl)sulfamoyl] phenyl ester of pivalic acid | Rf 0.42 (methylene chloride: ethyl acetate = 10:1) | ν 3450, 3250, 1730, 1590, 1480, 1430 |
| 2(16) | $-N$(piperidine-3-COOH); $-H$ | P-[(3-carboxy)piperidinosulfonyl] phenyl ester of pivalic acid | Rf 0.41 (chloroform: methanol: acetic acid = 100:5:1) | δ 7.8(2H, d), 7.3(2H, d), 4.0~3.4(3H, b), 3.0~1.3(6H, b), 1.35(9H, s) |
| 2(17) | $-NH-$phenyl; 2-CH$_3$ | 2-methyl-4-(N-phenylsulfamoyl) phenyl ester of pivalic acid | Rf 0.44 (hexane: ethyl acetate = 5:2) | δ 7.7~7.5(2H, m), 7.4~7.0(6H, m), 6.45(1H, bs), 2.2(3H, s), 1.35(9H, s) |
| 2(18) | $-N(CH_3)-$(o-carboxyphenyl); 2-CH$_3$ | 2-methyl-4-[N-methyl-N-(o-carboxy)sulfamoyl]phenyl ester of pivalic acid | Rf 0.43 (chloroform: methanol: acetic acid = 100:5:1) | δ 7.9(1H, dd), 7.7~7.0(6H, m), 3.35(3H, s), 2.2(3H, s), 1.4(9H, s) |
| 2(19) | $-N$(2S-carboxypyrrolidinyl); 2-CH$_3$ | 2-methyl-4-[(2S-carboxy-1-pyrrolidinyl)sulfonyl]phenyl ester of pivalic acid | Rf 0.26 (chloroform: methanol: acetic acid = 100:5:1) | δ 7.8(1H, s), 7.75(1H, d), 7.2(1H, d), 4.4~4.2(1H, m), 2.4~1.6(7H, m), 1.4(9H, m) |
| 2(20) | $-NH-CH_2-$(cyclohexyl-COOH, trans); 2-CH$_3$ | 2-methyl-4-[N-(p-carboxycyclohexanemethyl)sulfamoyl] phenyl ester of pivalic acid | Rf 0.40 (chloroform: methanol: acetic acid = 100:5:1) | δ 7.8(1H, s) 7.75(1H, d), 2.85(2H, d), 2.3(3H, s), 1.4(9H, s) |
| 2(21) | $-N$(piperidine-4-COOH); 2-CH$_3$ | 2-methyl-4-[(4-carboxyl)piperidinosulfonylphenyl ester of pivalic acid | Rf 0.36 (chloroform: methanol: acetic acid = 100:5:1) | δ 7.65(1H, s), 7.6 (1H, d), 3.8~3.4 (3H, b), 2.7~2.3 (2H, m), 2.25(3H, s), 2.2~1.6(5H, b), 1.4(9H, s) |
| 2(22) | $-N$(piperidine-3-COOH); 2-CH$_3$ | 2-methyl-4-[(3-carboxy)piperidinosulfonylphenyl ester of pivalic acid | Rf 0.36 (chloroform: methanol: acetic acid = 100:5:1) | δ 7.68(1H, s), 7.61 1H, d), 3.9~3.3 (2H, m), 2.8~2.4 (3H, m), 2.25(3H, s), 1.35(9H, s) |

TABLE IV-continued (CH₃)₃C—C(=O)—O—[phenyl(1,4) with (R³)ₘ]—SO₂—NR¹R²

| Example No. | —NR¹R² / —R³* | Name | TLC | IR (cm⁻¹) or NMR |
|---|---|---|---|---|
| 2(23) | —NH—(2-COOCH₃-phenyl); 2-CH₃ | 2-methyl-4-[(N-((o-methoxycarbonyl)phenyl)sulfamoyl]phenyl ester of pivalic acid | Rf 0.6 (methylene chloride: ethyl acetate = 30:1) | ν 3125, 2970, 1740, 1685, 1600, 1580, 1490, 1265, 1110, 940, 760 |
| 2(24) | —NH—(2-COOCH₃-phenyl); 2-CH₃ | 2-methyl-4-[N-((o-acetyl)phenyl)sulfamoyl]phenyl ester of pivalic acid | Rf 0.6 (methylene chloride: ethyl acetate = 30:1) | ν 2980, 1755, 1640, 1605, 1580, 1495, 1450, 1400, 1260, 1150, 1105 |
| 2(25) | —NH—(2-CONH₂-phenyl); 2-CH₃ | 2-methyl-4-[N-((o-aminocarbonyl)phenyl)sulfamoyl]phenyl ester of pivalic acid | Rf 0.1 (methylene chloride: ethyl acetate = 30:1) | ν 3450, 3200, 2970, 1730, 1670, 1615, 1575, 1490, 1340, 1280, 1220, 1150, 1110 |
| 2(26) | —N(piperidine with 2-COOH); 2-CH₃ | 2-methyl-4-[(2-carboxy)piperidinosulfonyl]phenyl ester of pivalic acid | Rf 0.41 (chloroform: methanol: acetic acid = 100:5:1) | δ 7.7(1H, d), 7.75 (1H, s), 7.1(1H, d), 4.8(1H, b), 3.8 (1H, b), 3.2(1H, b), 2.2(3H, s), 2~1.2(6H, b), 1.35(9H, s) |
| 2(27) | —NH—(2-OH-phenyl); 2-CH₃ | 2-methyl-4-[N-(o-phenyl)sulfamoyl]phenyl ester of pivalic acid | Rf 0.20 (hexane: ethyl acetate = 5:2) | δ 7.5(2H, b), 7.2~6.5(5H, m), 6.2(2H, b), 2.1(3H, s), 1.3(9H, s) |
| 2(28) | —NH—(2-COOCH₂CON(CH₃)₂-phenyl); 2-CH₃ | 2-methyl-4-[N-(o-(N,N-dimethylcarbamoylmethoxycarbonyl)phenyl)sulfamoyl]phenyl ester of pivalic acid | Rf 0.51 (chloroform: methanol: acetic acid = 100:5:1) | δ 1760, 1690, 1680, 1490, 1590, 1410, 1260, 1150, 1110 |
| 2(29) | —NH—(CH₂)₂COOH; 2-CH₃ | 2-methyl-4-[(N-carboxyethyl)sulfamoyl]phenyl ester of pivalic acid | Rf 0.33 (chloroform: methanol: acetic acid = 100:5:1) | (CDCl₃) δ 7.8(1H, s), 7.75 (1H, d), 7.15(1H, d), 5.7(1H, b), 3.25(2H, m), 2.6 (2H, t), 2.25(3H, s), 1.35(9H, s) |

TABLE IV-continued

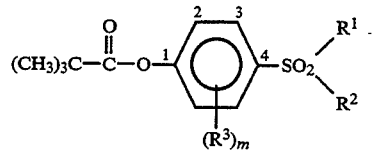

| Example No. | $-N\begin{smallmatrix}R^1\\R^2\end{smallmatrix}$ $-R^{3*}$ | Name | TLC | IR (cm$^{-1}$) or NMR |
|---|---|---|---|---|
| 2(30) | 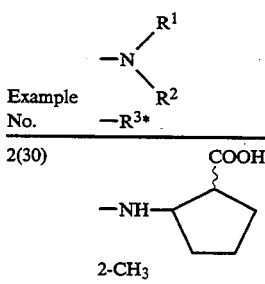 | 2-methyl-4-[N-(o-carboxycyclo-pentyl)sulfamoyl]phenyl ester of pivalic acid | Rf 0.33 (Chloroform: methanol = 10:1) | (CDCl$_3$) δ 7.8(1H, s), 7.75 (1H, d), 7.12(1H, d), 4.0~3.6(1H, b), 2.25(3H, s), 2.1~1.6(6H, b), 1.35(9H, s) |
| 2(31) | 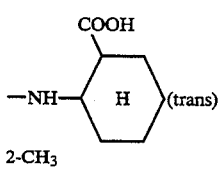 | 2-methyl-4-[N-(o-carboxycyclo-hexyl)sulfamoyl]phenyl ester of pivalic acid | Rf 0.33 (chloroform: methanol: = 10:1 | (CDCl$_3$) δ 7.65~7.90(2H, m), 7.1(1H, d), 2.25(3H, s), 1.4(9H, s), 1.0~3.0(10H, m) |
| 2(32) | 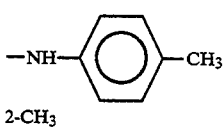 | 2-methyl-4-[N-(2-methoxy-5-carboxy)sulfamoyl]phenyl ester of pivalic acid | Rf 0.33 (chloroform: methanol: acetic acid = 100:5:1) | (CDCl$_3$) δ 8.18(1H, d), 7.8 (1H, d, d), 7.6(1H, s), 7.53(1H, d), 6.95(1H, d), 6.75 (1H, d), 3.65(3H, s), 2.2(3H, s), 1.35(9 H, s) |
| 2(33) | 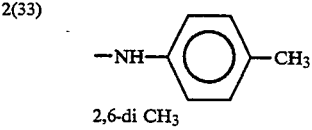 | 2.6-dimethyl-4-[N-(p-tolyl)sulfamoyl]phenyl ester of pivalic acid | Rf 0.44 (methylene chloride: ethyl acetate = 30:1) | ν 1750, 1470, 1390, 1330, 1280, 1140, 1100 |
| 2(34) | 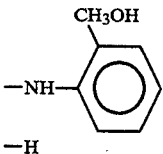 | 4-[N-(o-hydroxymethylphenyl)sulfamoyl]phenyl ester of pivalic acid | Rf 0.76 (ethyl acetate: hexane = 2:1) | ν 3470, 3050, 2950, 2850, 1750, 1590, 1470, 1320, 1210 |
| 2(35) | 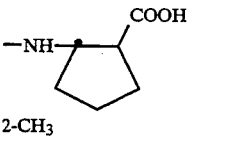 | 2-methyl-4-[N-(trans-o-carboxy-cyclopentyl)sulfamoyl]phenyl ester of pivalic acid | Rf 0.33 (chloroform: methanol: = 10:1) | (CDCl$_3$) δ 7.75(1H, s), 7.7 (1H, d), 7.1(1H, d), 3.75(1H, m), 2.5(1H, m), 2.25 (3H, s), 2.4~1.4 (6H, m), 1.4(9H, s) |
| 2(36) | 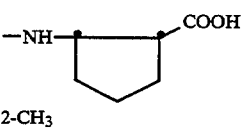 | 2-methyl-4-[N-(cis-o-carboxyl-cyclopentyl)sulfamoyl]phenyl ester of pivalic acid | Rf 0.33 (chloroform: methanol = 10:1) | (CDCl$_3$ + CD$_3$OD) δ 7.75(1H, s), 7.7 (1H, d), 7.1(1H, d), 3.75(1H, m), 2.8(1H, m), 2.25 (3H, s), 2.0~1.4 (6H, m), 1.4(9H, s) |
| 2(37) | 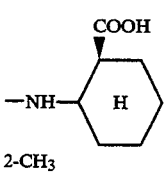 | 2-methyl-4-[N-cis-o-carboxy-cyclohexyl)sulfamoyl]phenyl ester of pivalic acid | Rf 0.18 (chloroform: methanol: = 10:1) | ν 3260, 2400~2700, 1740, 1700, 1470, 1420, 1330 |

TABLE IV-continued

Structure: $(CH_3)_3C-C(=O)-O-{}^{1}[C_6H_3(R^3)_m]{}^{4}-SO_2-NR^1R^2$ (positions 1,2,3,4 on phenyl ring)

| Example No. | $-N\begin{smallmatrix}R^1\\R^2\end{smallmatrix}$ / $-R^{3*}$ | Name | TLC | IR (cm⁻¹) or NMR |
|---|---|---|---|---|
| 2(38) | -NH-(2-CH₃-C₆H₄)- with COOCH₂CON(C₂H₅)₂ substituent; 2-CH₃ | 2-methyl-4-[N-(o-(N,N-diethyl-carbamoylmethoxycarbonyl)phehyl)sulfamoyl]phenyl ester of pivalic acid | Rf 0.55 (methylene chloride: ethyl acetate = 30:1) | ν 3160, 3000, 1755, 1670, 1590, 1490, 1270, 1100, 940 |
| 2(39) | -NH-(C₆H₄-SO₂NH₂); 2-CH₃ | 2-methyl-4-[N-(o-sulfamoylphenyl)sulfamoyl]phenyl ester of pivalic acid | Rf 0.20 (chloroform: methanol: acetic acid = 100:51:1) | ν 1750, 1720, 1590, 1570, 1460 |
| 2(40) | -NH-(C₆H₄-COOH); 2-CH₃ | 2-methyl-4-[N-(m-carboxyphenyl)sulfamoyl]phenyl ester of pivalic acid | Rf 0.33 (chloroform: methanol: acetic acid = 100:5:1) | (CDCl₃ + CD₃OD) δ 7.75~7.4(3H, m), 7.4~7.1(3H, m), 6.97(1H, d), 2.15(3H, s), 1.35(9H, s) |
| 2(41) | -NH-(C₆H₄-CH₂COOH); -H | 4-[N-(m-carboxymethylphenyl)sulfamoyl]phenyl ester of pivalic acid | Rf 0.33 (chloroform: methanol: acetic acid = 100:5:1) | (CDCl₃ + CD₃OD) δ 7.7(2H, d), 7.2~6.8(6H, m), 3.45(2H, s), 1.30(9H, s) |
| 2(42) | -NH-(C₆H₄-CH₂COOH); 2-CH₃ | 2-methyl-4-[N-(m-carboxymethyl-phenyl)sulfamoyl]phenyl ester of pivalic acid | Rf 0.31 (chloroform: methanol: acetic acid = 100:5:1) | (CDCl₃ + CD₃OD) δ 7.55(1H, s), 7.5(1H, d), 7.2~6.8(5H, m), 3.45(2H, s), 2.15(3H, s), 1.35(9H, s) |
| 2(43) | -NH-(C₆H₄-(CH₂)₂COOH); 2-CH₃ | 2-methyl-4-[N-(m-carboxyethylphenyl)sulfamoyl]phenyl ester of pivalic acid | Rf 0.31 (chloroform: methanol: acetic acid = 100:5:1) | (CDCl₃) δ 7.62(1H, s), 7.5(1H, d), 7.25~6.9(4H, m), 6.75(1H, b), 6.6(1H, b), 2.8(2H, t), 2.6(2H, t), 2.2(3H, s), 1.35(9H, s) |
| 2(44) | -NH-(2-Cl, 5-COOH-C₆H₃); 2-CH₃ | 2-methyl-4-[N-(2-chloro-5-carboxyphenyl)sulfamoyl]phenyl ester of pivalic acid | Rf 0.34 (chloroform: methanol: acetic acid = 100:5:1) | (CDCl₃ + CD₃OD) δ 8.2(1H, b), 7.8~7.45(3H, b), 7.3(1H, d), 7.0(1H, d), 2.2(3H, s), 1.35(9H, s) |

TABLE IV-continued

Structure: (CH₃)₃C—C(=O)—O—[position 1 of phenyl ring]—[positions 2,3]—[position 4]—SO₂—NR¹R², with (R³)ₘ on the ring.

| Example No. | —N(R¹)(R²), —R³* | Name | TLC | IR (cm⁻¹) or NMR |
|---|---|---|---|---|
| 2(45) | —NH—(phenyl with (CH₂)₂COOH at m-position), —H | 4-[N-(m-carboxyethylphenyl)sulfamoyl] phenyl ester of pivalic acid | Rf 0.27 (chloroform: methanol: acetic acid = 100:5:1) | (CDCl₃) δ 7.65(2H, d), 7.1(2H, d), 7.35~6.8(2H, m), 6.8~6.6(2H, m), 2.85(2H, t), 2.55 (2H, t), 1.35(9H, s) |
| 2(46) | —NH—(phenyl with SO₃H at m-position), 2-CH₃ | 2-methyl-4-[N-(m-sulfonyl)sulfamoyl] phenyl ester of pivalic acid | Rf 0.35 (chloroform: methanol: acetic acid = 10:3:1) | (CD₃SOCD₃) δ 7.7~7.6(2H, m), 7.4~6.9(5H, m), 2.15(3H, s), 1.30(9H, s) |
| 2(47) | —NH—(phenyl with SO₃H and CH₃ substituents: 2-sulfo-4-methyl), 2-CH₃ | 2-methyl-4-[N-(2-sulfo-4-methyl-phenyl)sulfamoyl]phenyl ester of pivalic acid | Rf 0.44 (chloroform: methanol: acetic acid = 10:3:1) | (CDCl₃ + CD₃OD) δ 7.9~7.5(3H, m), 7.5~6.9(3H, m), 2.3(3H, s), 2.2(3H, s), 1.35(9H, s) |
| 2(48) | —NH—(phenyl with OCH₂COOH at m-position), 2-CH₃ | 2-methyl-4-[N-(m-carboxymethoxyphenyl)sulfamoyl] phenyl ester of pivalic acid | Rf 0.39 (chloroform: methanol: acetic acid = 30:3:1) | (CDCl₃) δ 7.55(1H, s), 7.5(1H, d), 7.32~6.5(5H, m), 6.2(1H, bs), 4.45(2H, s), 2.2 (3H, s), 1.37(9H, s) |
| 2(49) | —NH—(naphthalene with 1,4-dioxa-2-carboxy-8-yl, COOH), 2-CH₃ | 2-methyl-4-[N-(1,4-dioxa-2-carboxy-8-yl-naphthalene)sulfamoyl]phenyl ester of pivalic acid | Rf 0.27 (chloroform: methanol: acetic acid = 30:3:1) | (CDCl₃) δ 7.6(1H, s), 7.5 (1H, d), 7.35(1H, d,), 7.2(1H, d, d), 6.9(1H, d), 6.85 (1H, d), 4.7(1H, s), 4.5(1H, d), 4.1(1H, d, d), 2.1(1H, s), 1.38(1H, s) |
| 2(50) | —NH—(phenyl with CONHCH₂COOH at m-position), 2-CH₃ | N-[m-(3-methyl-4-pivaloyloxy-benzene)sulfonylaminobenzoyl] glycine | Rf 0.26 (chloroform: methanol: acetic acid = 30:3:1) | (CDCl₃ + CD₃OD) δ 7.6~6.9(7H, m), 4.1(2H, s), 2.15(3H, s), 1.35(9H, s) |
| 2(51) | —NH—(phenyl with O—(CH₂)₃—COOH at o-position), 2-CH₃ | 2-methyl-4-[N-(o-carboxypropoxy-phenyl)sulfamoyl]phenyl ester of pivalic acid | Rf 0.45 (chloroform: methanol: acetic acid = 100:5:1) | (CDCl₃ + CD₃OD) δ 7.6~7.3(3H, m), 7.1~6.5(4H, m), 3.8(2H, t), 2.4 (2H, t), 2.15(3H, s), 2.02(2H, q), 1.35(9H, s) |

TABLE IV-continued (CH₃)₃C—C(=O)—O—[benzene ring positions 1,2,3,4 with (R³)ₘ]—SO₂—NR¹R²

| Example No. | —N(R¹)(R²)  —R³* | Name | TLC | IR (cm⁻¹) or NMR |
|---|---|---|---|---|
| 2(52) | —NH—[phenyl with 3-COOH, 5-COOH]; 2-CH₃ | 2-methyl-4-[N-(3, 5-dicarboxyphenyl) sulfamoyl]phenyl ester of pivalic acid | Rf 0.39 (chloroform: methanol: acetic acid = 30:3:1) | (CDCl₃ + CD₃OD) δ 8.38(1H, t), 7.98(2H, s), 7.8~7.6(2H, m), 7.06(1H, d), 2.2(3H, s), 1.38(9H, s) |
| 2(53) | —NH—[phenyl with o-CONHCH₂COOH]; 2-CH₃ | N-[0-(3-methyl-4-pivaloyloxy-benzene) sulfonylaminobenzoyl]glycine | Rf 0.41 (chloroform: methanol: acetic acid = 30:3:1) | ν 2970, 1740, 1630, 1600, 1520, 1480, 1390, 1330, 1260, 1230, 1150, 1090, 930, 760, 590 |
| 2(54) | —NH—[1,4-dioxa-2-tetrazolyl-8-yl-naphthalene]; 2-CH₃ | 2-methyl-4-[N-(1.4-dioxa-2-tetrazoyl-8-yl-naphthalene) sulfamoyl]phenyl ester of pivalic acid | Rf 0.46 (chloroform: methanol: acetic acid = 30:3:1) | (CDCl₃) δ 7.6(1H, s), 7.5(1H, d), 7.3~6.7(4H, m), 5.2(1H, fou), 4.5(2H, eig), 2.1(3H, s), 1.4(9H, s) |
| 2(55) | —NH—[phenyl with o-CONH—CH(COOH)—CH(CH₃)₂]; 2-CH₃ | N-[o-(3-methyl-4-pivaloyloxy-benzene)sulfonylaminobenzoyl]-L-valine | Rf 0.44 (chloroform: methanol: acetic acid = 100:5:1) | (CDCl₃) δ 7.80(1H, d), 7.32~7.2(4H, m), 7.15(1H, t), 7.0 (1H, d), 6.4(1H, d), 4.5(1H, q), 2.3 (1H, m), 2.1(3H, s), 1.35(9H, s) |
| 2(56) | —NH—[phenyl with o-CONHCH₂COOH, p-Cl]; 2-CH₃ | N-[5-chloro-2-(3-methyl-4-pivaoloyloxybenzene)sulfonylamino-benzoyl]glycine | Rf 0.29 (chloroform: methanol: acetic acid = 100:5:1) | (CDCl₃ + CD₃OD) δ 7.8~6.9(7H, m), 3.95(2H, s), 2.15(3H, s), 1.35(9H, s) |
| 2(57) | —NH—[phenyl with o-CONH—CH(CH₃)COOH]; 2-CH₃ | N-[o-(3-methyl-4-pivaloyloxy-benzene)sulfonylaminobenzoyl]-dl-alanine | Rf 0.24 (chloroform: methanol: acetic acid = 100:5:1) | (CDCl₃) δ 7.75(1H, d), 7.6 (1H, s), 7.65~7.4 (2H, m), 7.3~7.05 (2H, m), 7.3~7.05 (2H, m), 7.0(1H, d), 6.55(1H, d), 4.6(1H, q), 2.1 (3H, s), 2.5(3H, s), 1.35(9H, s) |

TABLE IV-continued

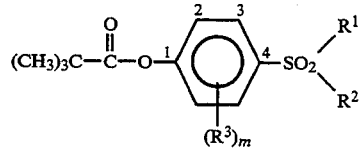

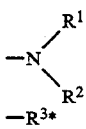

| Example No. | —R³* | Name | TLC | IR (cm⁻¹) or NMR |
|---|---|---|---|---|
| 2(58) | 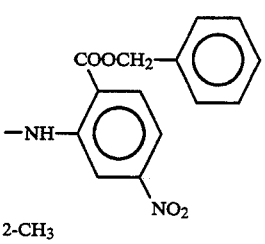 | N-[o-methyl-4-pivaloyloxy-benzene)sulfonylaminobenzoyl]-β-alanine | Rf 0.36 (chloroform: methanol: acetic acid = 100:5:1) | (CDCl₃) δ 7.75(1H, d), 7.6 (1H, s), 7.55~7.2 (3H, m), 7.1(1H, t), 6.95(1H, d), 6.6 (1H, b), 3.5(2H, q), 2.6(2H, q), 2.1(3H, s), 1.35(9H, s) |
| 2(59) | 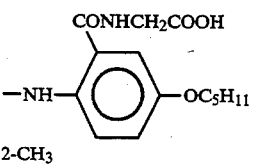 | 2-methyl-4-[N-(2-benzyloxycarbonyl-5-nitrophenyl)sulfamoylphenyl ester of pivalic acid | Rf 0.27 (ethyl acetate: hexane = 1:5) | (CDCl₃) δ 8.5(1H, d), 8.1(1H, d), 7.75(3H, m), 7.4(5H, s), 7.1(1H, d), 5.4(2H, s) |
| 2(60) | 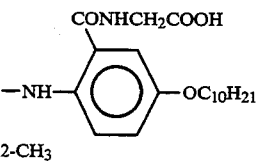 | N-[2-((3-methyl-4-pivaoyloxybenzene)sulfonylamino)-5-penthyloxybenzoyl]glycine | Rf 0.22 (ethyl acetate: hexane: acetic acid = 10:10:0.5) | (CD₃OD) δ 7.3~7.6(3H, m), 6.9~7.2(3H, m), 3.95(2H, t), 3.9(2H, t), 2.15(3H, s) |
| 2(61) | 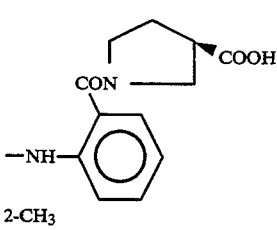 | N-[5-decyloxy-2-(3-methyl-4-pivaloyloxybenzene)sulfonylamino-benzoyl]glycine | Rf 0.25 (ethyl acetate: hexane: acetic acid = 10:10:0.5) | (CD₃OD) δ 7.35~7.6(3H, m), 6.9~7.2(2H, m), 3.95(2H, t), 3.9(2H, s), 2.1(3H, s) |
| 2(62) | 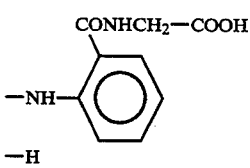 | 2-methyl-4-[N-(2-prolylcarbonylphenyl)sulfamoyl]phenyl ester of pivalic acid | Rf 0.18 (chloroform: methanol: acetic acid = 100:5:1) | (CDCl₃) δ 8.65(1H, s), 7.8~7.6(3H, m), 7.4~7.0(5H, m), 4.6(1H, m), 3.25(2H, t), 2.3~2.1(2H, m), 2.15(3H, s), 2.0~1.7(2H, m), 1.35 (9H, s) |
| 2(63) | 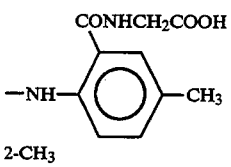 | N-[o-(p-pivaloyloxybenzene)sulfonylaminobenzoyl]glycine | Rf 0.14 (chloroform: methanol: acetic acid = 100:5:1) | (CDCl₃ + CD₃OD) δ 7.8~7.0(8H, m), 3.95(2H, s), 1.30(9H, s) |
| 2(64) | (structure with —NH—phenyl(2-CH₃)(CH₃), CONHCH₂COOH) | N-[2-(3-methyl-4-pivaloyloxybenzene)sulfonylamino-5-methylbenzoyl)glycine | Rf 0.20 (chloroform: methanol: acetic acid = 100:5:1) | (CDCl₃) δ 7.7~6.8(6H, m), 6.3(1H, b), 4.0(2H, d), 2.3(3H, s), 2.1(3H, s), 1.3(9H, s) |

TABLE IV-continued $(CH_3)_3C-\overset{O}{\underset{\|}{C}}-O-\overset{1}{\underset{(R^3)_m}{\bigcirc}}\overset{2\ 3}{\underset{4}{}}-SO_2-\overset{R^1}{\underset{R^2}{N}}$

| Example No. | $-N\overset{R^1}{\underset{R^2}{}}$ —R³* | Name | TLC | IR (cm⁻¹) or NMR |
|---|---|---|---|---|
| 2(65) | CH₃ on CONHCHCOOH; —NH—(phenyl, 2-CH₃) | N-[o-(3-methyl-4-pivaloyloxybenzene) sulfonylaminobenzoyl]-1-alanine | Rf 0.24 (chloroform: methanol: acetic acid = 100:5:1) | (CDCl₃) δ 7.8~6.9(7H, m), 6.5(1H, b), 4.6(1H, b), 2.1(3H, s), 1.45(3H, d), 1.35(9H, s) |
| 2(66) | CH₃ on CONHCHCOOH; —NH—(phenyl, 4-Cl, 2-CH₃) | N-[5-chloro-2-(3-methyl-4-pivaloyloxybenzene)sulfonylamino benzoyl]-1-alanine | Rf 0.3 (chloroform: methanol: acetic acid = 100:5:1) | (CDCl₃) δ 7.75(1H, d), 7.55 (1H, s), 7.5~7.3 (3H, m), 6.95(1H, d), 6.4(1H, b), 4.55(1H, m), 2.15 (3H, s), 1.45(3H, d), 1.35(9H, s) |
| 2(67) | CH₂—phenyl on CONHCHCOOH; —NH—(phenyl, 2-CH₃) | N-[o-(3-methyl-4-pivaloyloxybenzene) sulfonylaminobenzoyl]-L-phenylalanine | Rf 0.30 (ethyl acetate: hexane: acetic acid = 10:10:0.5) | (CD₃OD) δ 6.95~7.7(12H, m), 4.6~4.8(1H, m), 3.0~3.4(2H, m), 2.1(3H, s), 1.35(9H, s) |
| 2(68) | (CH₂)₂—SCH₃ on CONHCHCOOH; —NH—(phenyl, 2-CH₃) | N-[o-(3-methyl-4-pivaloyloxybenzene) sulfonylaminobenzoyl]-dl-methionine | Rf 0.29 (ethyl acetate: hexane: acetic acid = 10:10:0.5) | (CD₃OD) δ 7.55~7.8(4H, m), 7.45(1H, t), 7.0~7.2 (2H, m), 4.6~4.7(1H, m), 2.4~2.6(2H, m), s), 2.0~2.3(2H, m), 1.35(9H, s) |
| 2(69) | (CH₂)₄—NH₂ on CONHCCHCOOH; —NH—(phenyl, 2-CH₃)·HCl | N-[o-(3-methyl-4-pivaloyloxybenzene) sulfonylaminobenzoyl]-L-lysine. hydrochloride | Rf 0.73 (ethyl acetate: acetic acid: water = 3:1:0.5) | (CD₃OD) δ 7.57~7.80(3H, m), 7.0~7.22(2H, m), 4.45~4.65(1H, m), 2.95(2H, t), 2.15(3H, s), 1.4~2.1(6H, m), 1.35(9 H, s) |
| 2(70) | CONH—(phenyl-COOH); —NH—(phenyl, 2-CH₃) | 2-methyl-4-[N-(2-(N-carboxyphenyl-3-yl)carbamoylphenyl)sulfamoyl] phenyl ester of pivalic acid | Rf 0.52 (ethyl acetate: hexane: acetic acid = 10:10:0.5) | ν 1750, 1690, 1540, 1480, 1330, 1300, 1230, 1150, 1110 |

TABLE IV-continued

Structure:
(CH₃)₃C—C(=O)—O—[position 1 of phenyl ring]; phenyl ring positions 2,3; position 4—SO₂—NR¹R²; (R³)ₘ on ring

| Example No. | —N(R¹)(R²) / —R³* | Name | TLC | IR (cm⁻¹) or NMR |
|---|---|---|---|---|
| 2(71) | R¹/R²: —NH—(phenyl with OCH₂COOH); R³: 2-CH₃ | 2-methyl-4-[N-(2-carboxymethoxyphenyl)sulfamoyl]phenyl ester of pivalic acid | Rf 0.21 (chloroform: methanol: acetic acid = 30:3:1) | (CDCl₃) 4.5(2H, s), 2.15(3H, s), 1.3(9H, s) |
| 2(72) | R¹/R²: —NH—(phenyl with CONH(CH₂)₂COOH and Cl); R³: 2-CH₃ | N-[5-chloro-2-(3-methyl-4-pivaloyloxybenzene)sulfonylaminobenzoyl]-β-alanine | Rf 0.28 (chloroform: methanol: acetic acid = 100:5:1) | (CDCl₃) δ 7.8~7.2(5H, m), 7.0(1H, d), 7.6(1H, d), 3.6(2H, q), 2.64(2H, t), 2.2(3H, s), 1.35(9H, s) |
| 2(73) | R¹/R²: —NH—(phenyl with CONH(CH₂)₃COOH and Cl); R³: 2-CH₃ | 2-methyl-4-[N-((2-carboxypropylcarbamoyl-4-chloro)phenyl)sulfamoyl]phenyl ester of pivalic acid | Rf 0.28 (chloroform: methanol: acetic acid = 100:5:1) | (CDCl₃) δ 7.8~7.2(5H, m), 7.0(1H, d), 6.4(1H, b), 3.3(2H, q), 2.5(2H, t), 2.15(3H, s), 1.9(2H, m), 1.35(9H, s) |
| 2(74) | R¹/R²: —NH—(phenyl with CONH—phenyl—COOH); R³: 2-CH₃ | 2-methyl-4-[N-(2-(N-carboxyphenyl-4-yl)carbamoylphenyl)sulfamoyl]phenyl ester of pivalic acid | Rf 0.54 (ethyl acetate: hexane: acetic acid = 10:10:0.5) | ν 1750, 1680, 1650, 1590, 1520, 1480, 1400, 1320, 1280, 1250, 1220 |
| 2(75) | R¹/R²: —NH—(phenyl with CONHCH₂COOH and Cl); —H | N-[2-(p-pivaloyloxybenzene)sulfonylamino-5-chlorobenzoyl]glycine | Rf 0.23 (chloroform: methanol: acetic acid = 100:5:1) | (CDCl₃) δ 7.7(2H, d), 7.8~7.6(1H, m), 7.6~7.4(2H, m), 7.08(2H, d), 6.3(1H, b), 4.08(2H, d), 1.35(9H, s) |
| 2(76) | R¹/R²: —NH—(phenyl with CONHCHCOOH—CH₂—phenyl—OH); R³: 2-CH₃ | N0[o-(3-methyl-4-pivaloyloxybenzene)sulfonylaminobenzoyl[tyrosine | Rf 0.27 (ethyl acetate: hexane: acetic acid = 10:10:0.5) | (CD₃OD) δ 7.32~7.7(5H, m), 7.0~7.2(2H, m), 7.05(2H, d), 6.7(2H, d), 2.87~4.25(2H, m), 2.12(3H, s), 1.35(9H, s) |
| 2(77) | R¹/R²: —NH—(phenyl with CH₂CONHCH₂COOH); R³: 2-CH₃ | N-[o-(3-methyl-4-pivaloyloxybenzene)sulfonylaminophenylacetyl]glycine | Rf 0.44 (ethyl acetate: acetic acid = 25:1) | (CD₃OD) δ 7.5~7.7(2H, m), 7.0~7.35(5H, m), 3.9(2H, s), 3.37(2H, s), 2.2(3H, s), 1.41(9H, s) |

TABLE IV-continued $(CH_3)_3C-\overset{O}{\underset{\|}{C}}-O-\underset{(R^3)_m}{\underset{|}{\text{1}}}\text{C}_6\text{H}_3\text{-4-}SO_2-N\begin{matrix}R^1\\R^2\end{matrix}$ $-N\begin{matrix}R^1\\R^2\end{matrix}$

| Example No. | —R³* | Name | TLC | IR (cm⁻¹) or NMR |
|---|---|---|---|---|
| 2(78) | CH₂CONHCH₂COOH<br>—NH—C₆H₅<br>—H | N-[o-(4-pivaloyloxybenzene)sulfonylaminophenylacetyl]glycine | Rf 0.37<br>(ethyl acetate: acetic acid = 25:1) | ν 1750, 1610, 1530, 1480, 1400 |
| 2(79) | CONH(CH₂)₃COOH<br>—NH—C₆H₄—Cl<br>—H | 4-[N-((2-carboxypropylcarbamoyl-4-chloro)phenyl)sulfamoyl]phenyl ester of pivalic acid | Rf 0.47<br>(chloroform: methanol: acetic acid = 100:5:1) | (CDCl₃ + CD₃OD)<br>δ 7.7(2H, d), 7.5<br>(1H, s), 7.4~7.2<br>(2H, m), 7.1(2H, d),<br>3.2(2H, t),<br>2.3(2H, t),<br>1.8(2H, m),<br>1.3(9H, s) |
| 2(80) | CONHCH₂COOH<br>—NH—C₆H₄—SCH₃<br>—H | N-[5-methylthio-2-(p-pivaloyoxybenzene)sulfonylaminobenzoyl]glycine | Rf 0.34<br>(chloroform: methanol: acetic acid = 30:3:1) | (CDCl₃ + CD₃OD)<br>δ 7.7(2H, d),<br>7.6(1H, d),<br>7.4~7.2(2H, m),<br>7.1(2H, d),<br>3.98(2H, s),<br>2.5(3H, s),<br>1.4(9H, s) |
| 2(81) | CONHCH₂COOH<br>—NH—C₆H₃—CF₃<br>2-CH₃ | N-[2-(3-methyl-4-pivaloyloxybenzene)sulfonylamino-4-trifluoromethylbenzoyl]glycine | Rf 0.12<br>(ethyl acetate: hexane: acetic acid = 10:10:0.5) | (CD₃OD)<br>δ 7.92(1H, s), 7.80<br>(1H, d), 7.55~7.7<br>(2H, m), 7.45<br>(1H, d), 7.11(1H, d),<br>4.0(2H, s),<br>2.16(3H, s)<br>1.36(9H, s) |
| 2(82) | CONHCH₂COOH<br>—NH—C₆H₄—CF₃<br>—H | N-[2-(p-pivaloyloxybenzene)sulfonylamino-4-trifluoromethylbenzoyl]glycine | Rf 0.12<br>(ethyl acetate: hexane: acetic acid = 10:10:0.5) | (CD₃OD)<br>δ 7.95(1H, s),<br>7.77(2H, d),<br>7.80(1H, d),<br>7.45(1H, d),<br>7.20(2H, d),<br>4.0(2H, s),<br>1.33(9H, s) |
| 2(83) | CH₂—SCH₃<br>\|<br>CONHCHCOOH<br>—NH—C₆H₄—<br>—H | N-[o-(p-pivaloyoxybenzene)sulfonylaminobenzoyl]-S-methyl-L-cysteine | Rf 0.27<br>(chloroform: methanol: acetic acid = 100:5:1) | (CDCl₃ + CD₃OD)<br>δ 7.8(2H, d),<br>7.7~7.2(3H, m),<br>7.1(2H, d),<br>7.11(1H, d),<br>4.8(1H, m),<br>3.05(2H, m), 2.15<br>(3H, s), 1.3(9H, s) |
| 2(84) | (CH₂)₂—SCH₃<br>\|<br>CONHCHCOOH<br>—NH—C₆H₄—<br>—H | N-[2-(4-pivaloyloxybenzene)sulfonylaminobenzoyl]-L-methionine | Rf 0.34<br>(chloroform: methanol: acetic acid = 100:5:1) | (CDCl₃ + CD₃OD)<br>δ 7.8(2H, d),<br>7.7~7.2(3H, m),<br>7.1(2H, d),<br>7.11(1H, d),<br>4.7(1H, m), 2.8~2.0<br>(4H, m), 2.14(3H, s),<br>1.3(9H, s) |

TABLE IV-continued $$(CH_3)_3C-\overset{O}{\underset{\|}{C}}-O-\underset{(R^3)_m}{\overset{2\quad 3}{\underset{\phantom{x}}{\text{Ph}}}}-SO_2-\overset{R^1}{\underset{R^2}{N}}$$

| Example No. | $-N\overset{R^1}{\underset{R^2}{}}$  $-R^3*$ | Name | TLC | IR (cm$^{-1}$) or NMR |
|---|---|---|---|---|
| 2(85) | CONHCH$_2$COOH, —NH—[phenyl]—OC$_{10}$H$_{21}$, —H | N-[5-decyloxy-2-(p-pivaloyloxybenzene)sulfonylaminobenzoyl]glycine | Rf 0.49 (ethyl acetate: hexane: acetic acid = 10:10:0.5) | ν 3449, 2926, 1762, 1728, 1645, 1607, 1520, 1501, 1252 |
| 2(86) | CONHCH$_2$COOH, —NH—[phenyl]—S—CH$_3$, 2-CH$_3$ | N-[2-(3-methyl-4-pivaloyloxybenzene)sulfonylamino-5-methylthiobenzoyl]glycine | Rf 0.25 (chloroform: methanol: acetic acid = 100:5:1) | (CDCl$_3$ + CD$_3$OD) δ 7.7–7.2(5H, m), 6.95(1H, d), 2.95(2H, s), 2.5(3H, s), 2.2(3H, s), 1.35(9H, s) |
| 2(87) | CONHCH$_2$COOH, —NH—[phenyl]—S—(CH$_2$)$_2$CH$_3$, —H | N-[2-(p-pivaloyloxybenzene)sulfonylamino-5-propylthiobenzoyl]glycine | Rf 0.29 (chloroform: methanol: acetic acid = 100:5:1) | (CDCl$_3$ + CD$_3$OD) δ 7.75(2H, d), 7.6~7.1(3H, m), 7.1(2H, d), 4.0(2H, s), 2.9(2H, t), 1.8~1.5(2H, m), 1.35 (9H, s), 1.0(3H, t) |
| 2(88) | CONH—CHCOOH (phenyl), —NH—[phenyl], —H | N-[o-(p-pivaloyloxybenzene)sulfonylaminobenzoyl]-2R-phenylglycine | Rf 0.19 (ethyl acetate: hexane: acetic acid = 10:10:0.5) | (CD$_3$OD) δ 7.55–7.7(4H, m), 7.2–7.7(6H, m), 7.15(1H, t), 6.97(2H, d), 5.57(1H, s), 1.3(9H, s) |
| 2(89) | CONH—CHCOOH (phenyl), —NH—[phenyl], —2-CH$_3$ | N-[o-(3-methyl-4-pivaloyloxybenzene)sulfonylaminobenzoyl]-2R-phenylglycine | Rf 0.2 (ethyl acetate: hexane: acetic acid = 10:10:0.5) | (CD$_3$OD) δ 7.2~7.8(10H, m), 7.12(1H, t), 6.90(1H, d), 5.57(1H, s), 2.06(3H, s), 1.35(9H, s) |
| 2(90) | CONHCH$_2$COOH, —NH—[phenyl]—CH$_3$, —H | N-[5-methyl-2-(p-pivaloyloxybenzene)sulfonylamino-benzoyl]glycine | Rf 0.27 (chloroform: methanol: acetic acid = 100:5:1) | (CDCl$_3$ + CD$_3$OD) δ 7.7(2H, d), 7.5(1H, s), 7.3~7.1(2H, b), 7.0(2H, d), 3.95(2H, s), 2.3(3H, s), 1.3(9H, s) |
| 2(91) | CONH—[phenyl], —NH—[phenyl]—COOH, —H | 4-[N-(o-(N-carboxyphenyl-3-yl)carbamoylphenyl)sulfamoyl]phenyl ester of pivalic acid | Rf 0.32 (chloroform: methanol: acetic acid = 100:5:1) | ν 1752, 1692, 1646, 1595, 1554, 1491, 1409, 1338, 1304, 1259, 1209 |

TABLE IV-continued

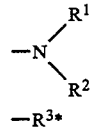

| Example No. | —R³* | Name | TLC | IR (cm⁻¹) or NMR |
|---|---|---|---|---|
| 2(92) | 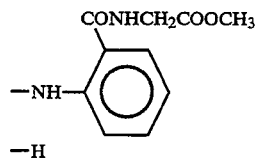 | N-[2-(p-pivaloyloxybenzene)sulfonylaminobenzoyl]glycine methyl ester | Rf 0.77 (chloroform: methanol: = 10:1) | (CDCl₃) δ 7.7(2H, d), 7.65(1H, b), 7.55~7.3(2H, m), 7.2~7.0(1H, m), 7.0(2H, d), 4.0(2H, d), 3.8 (3H, s), 1.35(9H, s) |
| 2(93) | 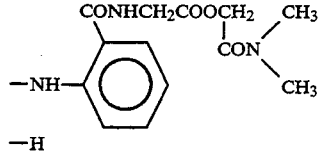 | 2-[N-(2-(4-pivaloyloxybenzene)sulfonylaminobenzoyl)glycyloxy]-N,N-dimethylacetamide | Rf 0.53 (chloroform: methanol = 10:1) | (CDCl₃) δ 7.7(2H, d), 7.8~7.6(1H, b), 7.55~7.2(2H, m), 7.2~7.0(1H, m), 7.05(2H, d), 4.8 (2H, s), 4.2(2H, d), 3.0(6H, s), 1.35(9H, s) |
| 2(94) | 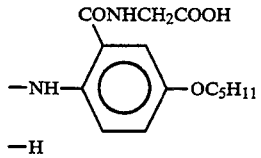 | N-[5-pentyloxy-2-(p-pivaloyloxybenzene)sulfonylaminobenzoyl]glycine | Rf 0.26 (ethyl acetate: hexane: acetic acid = 10:10:0.5) | (CDCl₃) δ 7.65(2H, d), 7.50 (1H, d), 7.18(2H, d), 7.11(1H, s), 7.02(1H, dd), 3.95(2H, t), 3.88 (2H, s), 1.65~1.85(2H, m), 1.25~1.55(4H, m), 1.33(9H, s), 1.92(3H, t) |
| 2(95) | 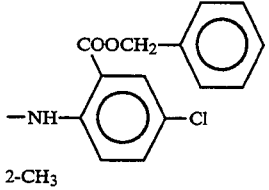 | 2-methyl-4-[N-((2-benzyloxy-carbonyl-4-chloro)phenyl)sulfamoyl]phenyl ester of pivalic acid | Rf 0.30 (ethyl acetate: hexane: = 1:10) | |
| 2(96) | 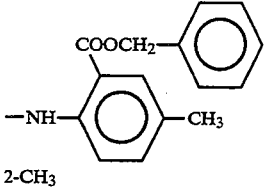 | 2-methyl-4-[N-((2-benzyloxy-carbonyl-4-methyl)phenyl)sulfamoyl]phenyl ester of pivalic acid | Rf 0.28 (ethyl acetate: hexane: = 1:10) | |
| 2(97) | 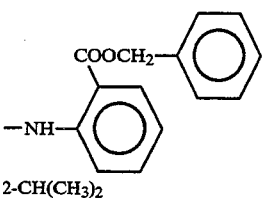 | 2-isopropyl-4-[N-(o-benzyloxycarbonylphenyl)sulfamoyl]phenyl ester of pivalic acid | Rf 0.32 (ethyl acetate: hexane: = 1:10) | |

TABLE IV-continued

Structure:
(CH₃)₃C—C(=O)—O—[phenyl with positions 1,2,3,4 and (R³)ₘ]—SO₂—NR¹R²

| Example No. | —NR¹R² / —R³* | Name | TLC | IR (cm⁻¹) or NMR |
|---|---|---|---|---|
| 2(98) | —NH-(2-COOCH₂Ph, 4-Cl-phenyl); 2-CH(CH₃)₂ | 2-isopropyl-4-[N-((2-benzyloxycarbonyl-4-chloro)phenyl)sulfamoyl]phenyl ester of pivalic acid | Rf 0.35 (ethyl acetate: hexane: = 1:10) | |
| 2(99) | —NH-(2-COOCH₂Ph-naphthyl); 2-CH₃ | 2-methyl-4-[N-(2-benzyloxycarbonyl-phenyl)sulfamoyl]phenyl ester of pivalic acid | Rf 0.58 (ethyl acetate: hexane: = 1:10) | |
| 2(100) | —NH-(2,5-di-COOCH₂Ph-phenyl); 2-CH₃ | 2-methyl-4-[N-(2,5-dibenzyloxy-carbonylphenyl)sulfamoyl]phenyl ester of pivalic acid | Rf 0.12 (ethyl acetate: hexane: = 1:10) | |
| 2(101) | —NH-(3-COOCH₂Ph-pyridyl); 2-CH₃ | 2-methyl-4-[N-(3-benzyloxycarbonylphenyl)sulfamoyl]phenyl ester of pivalic acid | Rf 0.37 (ethyl acetate: hexane: = 2:5) | |
| 2(102) | —NH-(2-COOCH₂Ph, 4-OH-phenyl); 2-CH₃ | 2-methyl-4-[N-((2-benzyloxycarbonyl-4-hydroxy)phenyl)sulfamoyl]phenyl ester of pivalic acid | Rf 0.18 (methylene chloride: methanol = 10:1) | |
| 2(103) | —NH-(2-COOCH₂Ph-phenyl); 2,6-diCH₃ | 2,6-dimethyl-4-[N-(o-benzylcarbonylphenyl)sulfamoyl]phenyl ester of pivalic acid | | |

TABLE IV-continued

Structure:

$(CH_3)_3C-\overset{O}{\underset{\|}{C}}-O-\underset{(R^3)_m}{\overset{2\ 3}{\underset{1\ \ \ \ 4}{\text{[phenyl]}}}}-SO_2-N\overset{R^1}{\underset{R^2}{}}$ Substituent: $-N\overset{R^1}{\underset{R^2}{}}$

| Example No. | —R³* | Name | TLC | IR (cm⁻¹) or NMR |
|---|---|---|---|---|
| 2(104) | (2-methyl-4-NH-phenyl with COOCH₂-phenyl and OCOCH₃ substituents); 2-CH₃ | 2-methyl-4-[N-((4-acetyloxy-2-benzyloxycarbonyl)phenyl)sulfamoyl] phenyl ester of pivalic acid | Rf 0.39 (chloroform: methanol = 10:1) | |
| 2(105) | (2-methyl-4-NH-phenyl with COOCH₂-phenyl and OCO(CH₂)₄CH₃); 2-CH₃ | 2-methyl-4-[N-((2-benzyloxycarbonyl-4-hexanoyloxy)phenyl)sulfamoyl] phenyl ester of pivalic acid | Rf 0.44 (mchloroform: methanol = 10:1) | |
| 2(106) | (2-methyl-4-NH-phenyl with two COOCH₂-phenyl groups); 2-CH₃ | 2-methyl-4-[N-(2,6-dibenzyloxy-carbonylphenyl)sulfamoyl]phenyl ester of pivalic acid | Rf 0.12 (hexane: ethyl acetate = 10:1) | |
| 2(107) | (2-methyl-NH-phenyl with COOCH₂—COOCH₂-phenyl); 2-CH₃ | o-(3-methyl-4-pivaloyloxybenzene) sulfonylaminobenzoyloxy acetic acid benzylester | Rf 0.41 (hexane: ethyl acetate = 5:2) | |
| 2(114) | (NH-phenyl with CONH-CH(phenyl)COOH); —H | N-[o-(p-pivaloyloxybenzene) suflonylaminobenzoyl]-2S-phenyl glycine | Rf 0.31 (ethyl acetate: hexane: acetic acid = 10:10:0.5) | ν 1751, 1641, 1594, 1520, 1493, 1456, 1398, 1340, 1275, 1207, 1164, 1104 |

TABLE IV-continued

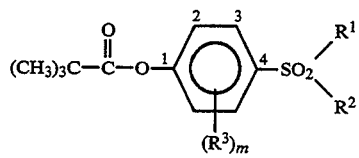

| Example No. | —R³* | Name | TLC | IR (cm⁻¹) or NMR |
|---|---|---|---|---|
| 2(115) | CONHCHCOOH / CH₂CH(CH₃)₂ ; —NH—⌬ ; —H | N-[o-(p-pivaloyloxybenzene)suflonylaminobenzoyl]-L-leucine | Rf 0.45 (Chloroform: methanol: acetic acid = 100:5:1) | (CDCl₃) δ 7.75(2H, d), 7.85~7.60(1H, m), 7.6~7.15(3H, m), 7.05(2H, d), 6.40 (1H, b), 5.4(1H, b), 4.6(1H, m), 2.0~1.4 (3H, b), 1.35(9H, s), 1.0(6H, d) |
| 2(116) | CONHCH₂CONH₂ ; —NH—⌬ ; —H | N-[o-(p-pivaloyloxybenzene)sulfonylaminobenzoyl]glycinamide | Rf 0.28 (chloroform: methanol: acetic acid = 100:5:1) | (CDCl₃ + CD₃OD + CD₃SOCO₃) δ 7.75(2H, d), 7.65~7.35(3H, m), 7.1(2H, d), 7.2~7.0(1H, b), 3.95(2H, s), 1.35(9H, s) |
| 2(117) | CONHCCHCOOH / CH₃ ; —NH—⌬ ; —H | N-[o-(p-pivaloyloxybenzene)sulfonylaminobenzoyl]-L-alanine | Rf 0.28 (chloroform: methanol acetic acid = 100:5:1) | (CDCl₃) δ 7.75(2H, d), 7.8~7.7(1H, b), 7.5~7.4(2H, m), 7.05(2H, d), 7.2~ 7.1(1H, m), 6.5(1H, d), 4.6(1H, q), 1.5 (3H, d), 1.35(9H, s) |
| 2(118) | CONH(CH₂)₂COOH ; —NH—⌬ ; —H | N-[o-(p-pivaloyloxybenzene)sulfonylaminobenzoyl]-β-alanine | Rf 0.48 (Chloroform: methanol: acetic acid = 100:5:1) | (CDCl₃) δ 7.7(2H, d), 7.8~7.7(1H, b), 7.45(1H, t), 7.3 (1H, d), 7.2(1H, t), 7.1(1H, d), 7.05 (2H, d), 6.6(1H, b), 3.5(2H, q), 2.6 (2H, t), 1.35(9H, s) |
| 2(119) | O(CH₂)₂COOH ; —NH—⌬ ; —H | p-[N-(o-carboxyethoxyphenyl)sulfamoyl]phenyl ester of pivalic acid | Rf 0.36 (chloroform: methanol: acetic acid = 100:5:1) | (CDCl₃) δ 7.7(2H, d), 7.75~7.65(1H, b), 7.2~7.0(5H, m), 6.8(1H, d), 4.0(2H, t), 2.6(2H, t), 1.35(9H, s) |
| 2(120) | CH(CH₃)₂ \ CONH—COOH ; —NH—⌬ ; —H | N-[o-(p-pivaloyloxybenzene)sulfonylaminobenzoyl]-S-valine | Rf 0.34 (acetic acid: chloroform = 1:19) | ν 2972, 1752, 1640, 1595, 1527, 1492, 1398 |

TABLE IV-continued

Structure: $(CH_3)_3C-C(=O)-O-$ [phenyl with positions 1,2,3,4, where position 1 bears the pivaloyloxy group, position 4 bears $-SO_2-NR^1R^2$, and $(R^3)_m$ substituents]

General amine substituent: $-N(R^1)(R^2)$

| Example No. | $-R^{3*}$ | Name | TLC | IR (cm$^{-1}$) or NMR |
|---|---|---|---|---|
| 2(121) | O(CH$_2$)$_3$COOH; —NH—phenyl; —H | p-[N-(o-carboxypropoxyphenyl) sulfamoyl]phenyl ester of pivalic acid | Rf 0.48 (Chloroform: methanol: acetic acid = 100:5:1) | (CDCl$_3$) δ 7.7(2H, d), 7.45(1H, d, d), 7.0(2H, d), 7.1~6.5(5H, m), 3.8(2H, t), 2.4(2H, t), 2.0(2H, b), 1.35(9H, s) |
| 2(122) | phenyl with ortho CON(CH$_3$)(CH$_2$COOH); —NH—; —H | N-methyl-N-[o-(p-pivaloyloxybenzene) sulfonylaminobenzoyl]glycine | Rf 0.17 (chloroform: methanol: acetic acid = 100:5:1) | (CDCl$_3$ + CD$_3$OD + D$_2$O) δ 7.8(2H, d), 7.8~7.5(1H, b), 7.1(2H, d), 7.4~7.0(4H, m), 4.1(2H, s), 2.7(3H, s), 1.35(9H, s) |
| 2(123) | phenyl with ortho CONHCH(CH$_2$Ph)COOH; —NH—; —H | N-[o-(p-pivaloyloxybenzene) sulfonylaminobenzoyl]-L-phenylalanine | Rf 0.36 (chloroform: methanol: acetic acid = 100:5:1) | (CDCl$_3$ + CD$_3$OD) δ 7.7(2H, d), 7.6(1H, d), 7.05(2H, d), 7.4~6.8(8H, m), 4.8(1H, b), 3.2(2H, m), 1.35(9H, s) |
| 2(124) | phenyl with ortho CONHCH(CH$_2$Ph)COOH (D-isomer); —NH—; —H | N-[o-(p-pivaloyloxybenzene) sulfonylaminobenzoyl]-D-phenylalanine | Rf 0.36 (Chloroform: methanol: acetic acid = 100:5:1) | (CDCl$_3$ + CD$_3$OD) δ 7.7(2H, d), 7.6(1H, d), 7.05(2H, d), 7.4~6.8(8H, m), 4.8(1H, b), 3.2(2H, m), 1.35(9H, s) |
| 2(125) | phenyl with ortho CONHCH(CH$_2$-indolyl)COOH; —NH—; —H | N-[o-(p-pivaloyloxybenzene) sulfonylaminobenzoyl]-L-tryptophan | Rf 0.25 (chloroform: methanol: acetic acid = 100:5:1) | (CDCl$_3$ + CD$_3$OD) δ 7.75(2H, d), 7.6(1H, d), 7.0(2H, d), 7.6~6.8(9H, m), 4.85(1H, b), 3.35(2H, d), 1.35(9H, s) |
| 2(126) | phenyl with ortho CONHCH$_2$COOH; —N(CH$_3$)—; —H | N-[o-(N-methyl-N-(p-pivaloyloxybenzene) sulfonylaminobenzoyl)]glycine | Rf 0.46 (chloroform: methanol:THF = 30:3:1) | ν 3391, 2977, 1756, 1662, 1597, 1535, 1482, 1405 |

TABLE IV-continued

[Structure: (CH₃)₃C-C(=O)-O-1-[benzene ring with positions 2,3]-4-SO₂-NR¹R², with (R³)ₘ substituent]

| Example No. | −R³*  −N(R¹)(R²) | Name | TLC | IR (cm⁻¹) or NMR |
|---|---|---|---|---|
| 2(127) | R³: −NH−[phenyl]−CONHCH(CH₂COOH)(−phenyl); R¹=H, R²=H | dl-3-phenyl-3-[o-(p-pivaloyloxybenzene)suflonylaminobenzoyl]amino propionic acid | Rf 0.5 (Chloroform:methanol:acetic acid = 100:5:1) | (CDCl₃ + CD₃OD) δ 7.6(2H, d), 7.7∼7.5(1H, m), 7.5∼7.1(7H, m), 7.0(1H, d, d), 6.9(2H, d), 5.5(1H, b), 2.9(2H, d), 1.35(9H, s) |
| 2(128) | R³: −NH−[phenyl]−CON[piperidine-4-COOH]; R¹=H, R²=H | N-[o-(p-pivaloyloxybenzene)sulfonylaminobenzoyl]-4-piperidine carboxylic acid | Rf 0.5 (chloroform:methanol:acetic acid = 100:5:1) | (CDCl₃ + CD₃OD) δ 7.7(1H, d), 7.6∼7.4(1H, m), 7.4∼7.2(1H, m), 7.2∼6.9(4H, m), 4.0∼3.6(1H, b), 2.9-2.4(4H, b), 2.0∼1.4(4H, b), 1.35(9H, s) |
| 2(129) | R³: −NH−[phenyl]−CONHCH[(CH₂)₂SCH₃]COOH; R¹=H, R²=H | N-[o-(p-pivaloyloxybenzene)sulfonylaminobenzyl]-D-methionine | Rf 0.45 (chloroform:methanol acetic acid = 100:5:1) | (CDCl₃ + CD₃OD) δ 7.8(2H, d), 7.7∼7.1(4H, m), 7.1(2H, d), 4.7(1H, b), 2.9(3H, s), 2.6∼1.9(4H, m), 1.35(9H, s) |
| 2(130) | R³: −NH−[phenyl]−CONHCH[CH(CH₃)₂]COOH; R¹=H, R²=H | N-[o-(p-pivaloyloxybenzene)sulfonylaminobenzoyl]-D-valine | Rf 0.46 (ethyl acetate:n-hexane:acetic acid = 10:10:0.5) | ν 3392, 2973, 1746, 1641, 1595, 1528, 1493, 1398 |
| 2(131) | R³: −NH−[phenyl]−CONH(CH₂)₃COOH; R¹=H, R²=H | p-[N-(o-carboxypropylcarbamoylphenyl)sulfamoyl]phenyl ester of pivalic acid | Rf 0.36 (chloroform:methanol:acetic acid = 100:5:1) | (CDCl₃ + CD₃OD) δ 7.7(2H, d), 7.7∼7.5(1H, b), 7.4∼7.2(2H, m), 7.0(2H, d), 7.1 (1H, d), 3.3(2H, t), mx,1 2.4(2H, t), 1.9 (2H, q), 1.35(9H, s) |
| 2(132) | R³: −NH−[phenyl]−CONH(CH₂)₅COOH; R¹=H, R²=H | p-[N-(o-carboxyheptylcarbamoylphenyl)sulfamoyl]phenyl ester of pivalic acid | Rf 0.38 (chloroform:methanol acetic acid = 100:5:1) | (CDCl₃ + CD₃OD) δ 7.7(2H, d), 7.7∼7.6(1H, b), 7.4∼7.2(2H, m), 7.0(2H, d), 7.1 (1H, b), 3.2(2H, b), 2.3(2H, b), 1.9∼1.2 (6H, b), 1.35(9H, s) |

TABLE IV-continued $$(CH_3)_3C-\overset{O}{\underset{\|}{C}}-O-\underset{(R^3)_m}{\overset{2\phantom{xx}3}{\underset{1\phantom{xxxx}4}{\bigcirc}}}-SO_2-N\overset{R^1}{\underset{R^2}{\diagdown}}$$

| Example No. | $-N\diagup^{R^1}_{\diagdown R^2}$ $-R^{3*}$ | Name | TLC | IR (cm$^{-1}$) or NMR |
|---|---|---|---|---|
| 2(133) | $-NH-\bigcirc\text{-CONHCH(CH}_3\text{)COOH}$ <br> $-H$ | N-[o-(p-pivaloyloxybenzene)sulfonylaminobenzoyl]-D-alanine | Rf 0.28 (chloroform: methanol: acetic acid = 100:5:1) | (CDCl$_3$ + CD$_3$OD)) δ 7.75(2H, d), 7.8~7.7(1H, b), 7.5~7.4(2H, m), 7.05(2H, d), 7.2~7.1(1H, m), 4.6(1H, m), 1.5(3H, d), 1.35(9H, s) |
| 2(134) | $-N\underset{\text{piperidine-COOH}}{\diagdown}$ <br> $-H$ | N-[(p-pivaloyloxybenzene)sulfonyl]-4-piperidine carboxylic acid | Rf 0.4 (chloroform: methanol: acetic acid = 100:5:1) | (CDCl$_3$) δ 7.75(2H, d), 7.2(2H, d), 3.6~(2H, b), 2.7~2.0(3H, m), 2.0~1.6(4H, m), 1.20(9H, s) |
| 2(135) | $-NH-\text{naphthyl-COOH}$ <br> $-H$ | 4-[(p-pivaloyloxybenzene)sulfonylamino]-2-naphtoic acid | Rf 0.4 (chloroform: methanol: acetic acid = 100:5:1) | (CDCl$_3$) δ 8.9(1H, d), 8.1(1H, d), 7.75(2H, d), 8.0~7.8(1H, b), 7.6~7.3(3H, m), 7.0(2H, d), 1.35(9H, s) |

*The number of the carbon atoms of benzene ring were named from a carbon atom conbined with the oxygen atom in pivaloyl group as first.

TABLE V $$(CH_3)_3C-\overset{O}{\underset{\|}{C}}-O-\underset{(R^3)_m}{\overset{2\phantom{xx}3}{\underset{1\phantom{xxxx}4}{\bigcirc}}}-CO-N\overset{R^1}{\underset{R^2}{\diagdown}}$$

| Example No. | $-N\diagup^{R^1}_{\diagdown R^2}$ $-R^{3*}$ | Name | TLC | IR (cm$^{-1}$) or NMR |
|---|---|---|---|---|
| 2(108) | $-NH-\bigcirc-CH_3$ <br> 2-Cl | 2-chloro-4-[N-(p-tolyl)carbamoyl]phenyl ester of pivalic acid | Rf 0.77 (methylene chloride: acetic acid = 30:1) | (CDCl$_3$) δ 7.5(2H, b), 7.2~6.5(5H, m), 6.2(2H, b), 2.1(3H, s), 1.3(9H, s) |
| 2(109) | $-NH-\bigcirc-CH_3$ <br> 2-OCH$_3$ | 2-methoxy-p-[N-(p-tolyl)carbamoyl]phenyl ester of pivalic acid | Rf 0.74 (methylene chloride: acetic acid = 30:1) | ν 3200, 2980, 1750, 1640, 1600, 1510, 1400, 1330, 1280, 1110 |

TABLE V-continued

Structure: $(CH_3)_3C-C(=O)-O-[phenyl(R^3)_m]-CO-N(R^1)(R^2)$ with positions 1, 2, 3, 4 on the phenyl ring.

| Example No. | $-N(R^1)(R^2)$, $-R^{3*}$ | Name | TLC | IR (cm$^{-1}$) or NMR |
|---|---|---|---|---|
| 2(110) | $-NH-$(phenyl with COOCH$_2$-phenyl); $-H$ | 4-[N-(o-benzyloxycarbonylphenyl)carbamoyl]phenyl ester of pivalic acid | Rf 0.83 (methylene chloride: acetic acid = 30:1) | |
| 2(111) | $-NH-$(2-pyridyl); $-H$ | 4-[N-(2-pyridyl)carbamoyl]phenyl ester of pivalic acid | Rf 0.30 (chloroform: methanol = 10:1) | |
| 2(112) | $-N(CH_3)-$phenyl; 3-OCOCH$_3$ | 3-acetyloxy-4-[(N-methyl-N-phenyl)carbamoyl]phenyl ester of pivalic acid | Rf 0.24 (methylene chloride: acetic acid = 30:1) | (CHDl$_3$) δ 7.1~7.5(6H, m), 6.7~7.0(2H, m), 3.5(3H, s), 2.3(3H, s), 1.3(9H, s) |
| 2(113) | $-NH-$(phenyl with COOCH$_2$-phenyl); $-H$ | 4-[N-(m-benzyloxycarbonylphenyl)carbamoyl]phenyl ester of pivalic acid | Rf 0.38 (methylene chloride: acetic acid = 30:1) | |

Example 3 p-[N-(p-(p-guanidinobenzoyloxy)phenyl)sulfamoyl]phenyl ester of pivalic acid

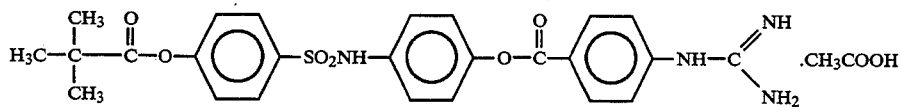

p-Guanidinobenzoyl chloride hydrochloride (800 mg) was added to pyridine solution (5 ml) of the compound of the present invention (500 mg) obtained in Example 2(7) under cooling with ice, and the mixture was stirred for 2 hours.

After reaction, ether was added to the reaction mixture and the supernatant was decanted. Saturated aqueous solution of sodium bicarbonate was added to the residue to obtain oily carbonate.

Further, tile supernatant was decanted and the residue was purified by column chlomatography on silicagel (ethyl acetate:acetic acid:water=400:100:30) to give the title compound (532 mg) having the following physical data.

TLC:Rf 0.80 (ethyl acetate:acetic acid:water=3:1:1); IR:γ3600~2300, 1750~1700, 1680, 1500, 1400.

Example 4 p-[N-(p-benzyloxycarbonylphenyl)sulfamoyl]phenyl ester of pivalic acid

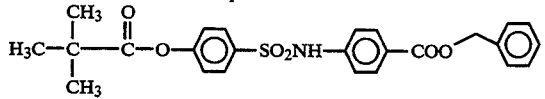

The title compound (210 mg, same as compound obtained in Example 1(5)) was obtained by tile same procedure as Reference Example 1 →Example 1, by using a corresponding sulfonylchloride compound as starting material.

The compounds of the present invention were obtained by the same procedure as Example 4, by using a corresponding amine and pivaloyl chloride.

TABLE VI

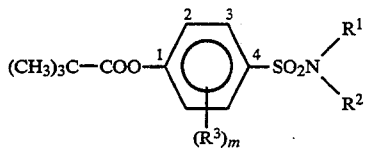

| Example No. | -N(R¹)(R²) / -R³* | Name | TLC | IR (cm⁻¹) or NMR |
|---|---|---|---|---|
| 4(1) | -NH-CH(COOCH₂Ph)(CH₂Ph) ; -H | p-[N-((1-benzyloxycarbonyl-1-benzyl)methyl)sulfamoyl]phenyl ester of pivalic acid | Rf 0.47 (hexane: ethyl acetate = 5:2) | |
| 4(2) | -NH-CH(COOCH₂Ph)(Ph) ; -H | p-[N-((1-benzyloxycarbonyl-1-phenyl)methyl)sulfamoyl]phenyl ester of pivalic acid | Rf 0.40 (hexane: ethyl acetate = 5:2) | |
| 4(3) | -NH(o-C₆H₄-COOCH₂Ph) ; -H | p-[N-((o-benzyloxycarbonyl)phenyl)sulfamoyl]phenyl ester of pivalic acid | Rf 0.62 (hexane: ethyl acetate = 5:2) | |
| 4(4) | -NH(o-C₆H₄-COOCH₂Ph) ; 2-CH₃ | 2-methyl-4-[N-((o-benzyloxycarbonyl)phenyl)sulfamoyl]phenyl ester of pivalic acid | Rf 0.62 (hexane: ethyl acetate = 5:2) | |
| 4(5) | -NH-(CH₂)₂-Ph ; -H | p-(N-phenethylsulfamoyl)phenyl ester of pivalic acid | Rf 0.41 (hexane: ethyl acetate = 5:2) | δ 7.85(2H, d), 7.4~7.0(7H, m), 4.5~4.2(1H, b), 3.4~3.1(2H, m), 2.8(2H, t), 1.35(9H, s) |
| 4(6) | -NH-CH₂-Ph ; -H | p-(N-benzylsulfamoyl)phenyl ester of pivalic acid | Rf 0.47 (hexane: ethyl acetate = 5:2) | δ 7.9(2H, d), 7.4~7.2(7H, m), 4.7(1H, b), 4.2(2H, d), 1.35(9H, s) |

Example 5 p-[N-(p-carboxyphenyl)sulfamoyl]phenyl ester of pivalic acid

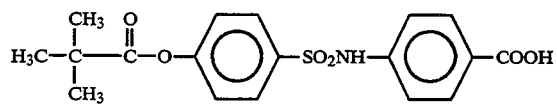

In an atmosphere of hydrogen gas, the mixture solution of benzyl compound (190 mg) of Example 4, 10% Pd-carbon (30 mg), acetic acid (10 ml) and THF (4 ml) was stirred for 3 hours at room temperature.

The reaction solution was filtered off, and the filtrate was carried out azeotropic concentration by mixture of toluene-THF, and the azeotropic concentrate was recrystallized by mixture of ethyl acetate-hexane to give title compound (143 mg) having the following physical data.

TLC:Rf 0.56 (ethyl acetate:hexane=1:1);

IR:γ 2700~2400, 1750, 1680, 1600, 1340, 1290, 1200, 1160, 1110 cm$^{-1}$.

Hereinafter, by the same procedure of Example 5, using corresponding benzyl compound, compounds of the present invention described in the following Table VII were obtained.

TABLE VII

Structure: $(CH_3)_3C-C(=O)-O-1-[phenyl\ ring\ with\ positions\ 2,3,4\ and\ (R^3)_m]-4-SO_2N(R^1)(R^2)$

| Example No. | $-N(R^1)(R^2)$, $-R^{3*}$ | Name | TLC | IR (cm$^{-1}$) or NMR |
|---|---|---|---|---|
| 5(1) | −NH−CH(COOH)(CH$_2$−Ph); −H | p-[N-(α-carboxyphenethyl)sulfamoyl] phenyl ester of pivalic acid | Rf 0.34 (chloroform: methanol: acetic acid = 100:5:1) | δ 7.8(2H, d), 7.4~7.0(7H, m), 5.2(1H, b), 4.2(1H, b), 3.2~3.0(2H, b), 1.4(9H, s) |
| 5(2) | −NH−CH(COOH)(Ph); −H | p-[N-(α-carboxybenzyl)sulfamoyl] phenyl ester of pivalic acid | Rf 0.44 (chloroform: methanol: acetic acid = 100:5:1) | δ 7.8(2H, d), 7.35(5H, bs), 7.15(2H, d), 5.75(1H, d), 5.15(1H, d), 1.35(9H, s) |
| 5(3) | −NH−(o-COOH-phenyl); −H | p-[N-(o-carboxyphenyl)sulfamoyl] phenyl ester of pivalic acid | Rf 0.37 (chloroform: methanol: acetic acid = 100:5:1) | δ 8.2~7.0(8H, m), 5.5(1H, b), 1.35(9H, s) |
| 5(4) | −NH−(o-COOH-phenyl); 2-CH$_3$ | 2-methyl-4-[N-(o-carboxyphenyl)sulfamoyl]phenyl ester of pivalic acid | Rf 0.25 (chloroform: methanol: acetic acid = 100:5:1) | δ 8.05(1H, d), 7.9~7.3(5H, m), 7.3~7.0(2H, m), 2.2(3H, s), 1.35(9H, s) |
| 5(5) | −NH−(2-COOH-4-Cl-phenyl); 2-CH$_3$ | 2-methyl-4-[N-(2-carboxy-4-chlorophenyl)sulfamoyl]phenyl ester of pivalic acid | Rf 0.26 (chloroform: methanol: acetic acid = 100:5:1) | (CDCl$_3$ + CD$_3$OD) δ 8.0(1H, d), 7.8~7.6(3H, m), 7.45(1H, d, d), 7.1(1H, d), 2.2(3H, s), 1.4(9H, s) |
| 5(6) | −NH−(2-COOH-4-CH$_3$-phenyl); 2-CH$_3$ | 2-methyl-4-[N-(2-carboxy-4-methylphenyl)sulfamoyl]phenyl ester of pivalic acid | Rf 0.41 (chloroform: methanol: acetic acid = 100:5:1) | (CDCl$_3$) δ 7.9~7.5(4H, m), 7.38(1H, d), 7.1(1H, d), 2.35(3H, s), 2.2(3H, s), 1.35(9H, s) |

TABLE VII-continued

Structure:
$(CH_3)_3C-C(=O)-O-\text{[phenyl(1,2,3,4 positions, with }(R^3)_m\text{)]}-SO_2N R^1 R^2$

| Example No. | $-N\begin{smallmatrix}R^1\\R^2\end{smallmatrix}$ / $-R^{3*}$ | Name | TLC | IR (cm$^{-1}$) or NMR |
|---|---|---|---|---|
| 5(7) | −NH−(phenyl with COOH ortho, 2-CH(CH$_3$)$_2$) | 2-isopropyl-4-[N-(o-carboxyphenyl)sulfamoyl]phenyl ester of pivalic acid | Rf 0.32 (chloroform: methanol: acetic acid = 100:5:1) | (CDCl$_3$) δ 8.0(1H, d), 7.9∼7.5(4H, m), 7.25(1H, d), 7.1(1H, d), 3.0(1H, b), 1.35(9H, s), 1.15(6H, d) |
| 5(8) | −NH−(phenyl with COOH and Cl, 2-CH(CH$_3$)$_2$) | 2-isopropyl-4-[N-(2-carboxy-4-chlorophenyl)sulfamoyl]phenyl ester of pivalic acid | Rf 0.32 (chloroform: methanol: acetic acid = 100:5:1) | (CDCl$_3$) δ 7.95(1H, d), 7.85∼7.4(4H, m), 7.05(1H, d), 3.0(1H, b), 1.35(9H, s), 1.15(6H, d) |
| 5(9) | −NH−(naphthyl with COOH, 2-CH$_3$) | 2-methyl-4-[N-(2-carboxynaphthyl)sulfamoyl]phenyl ester of pivalic acid | Rf 0.33 (chloroform: methanol: acetic acid = 100:5:1) | (CDCl$_3$) δ 8.6(1H, s), 8.05(1H, s), 7.9∼7.3(6H, m), 7.0(1H, d), 2.1(3H, s), 1.35(9H, s) |
| 5(10) | −NH−(phenyl with 2,5-di-COOH, 2-CH$_3$) | 2-methyl-4-[N-(2,5-dicarboxyphenyl)sulfamoyl]phenyl ester of pivalic acid | Rf 0.26 (chloroform: methanol: acetic acid = 30:2:1) | (CDCl$_3$ + CD$_3$OD) δ 8.3(1H, d), 8.0(1H, d), 7.8∼7.6(3H, m), 7.03(1H, d), 2.2(3H, s), 1.35(9H, s) |
| 5(11) | −NH−(pyridine with COOH, 2-CH$_3$) | 2-methyl-4-[N-(3-carboxypyridine-2-yl)sulfamoyl]phenyl ester of pivalic acid | Rf 0.48 (chloroform: methanol: acetic acid = 30:2:1) | (CDCl$_3$ + CD$_3$OD) δ 8.3(2H, m), 8.0(1H, s), 7.9(1H, d), 6.95(1H, d, d), 2.25(3H, s), 1.35(9H, s) |
| 5(12) | −NH−(phenyl with COOH and OH, 2-CH$_3$) | 2-methyl-4-[N-(2-carboxy-4-hydroxyphenyl)sulfamoyl]phenyl ester of pivalic acid | Rf 0.31 (chloroform: methanol: acetic acid = 30:2:1) | (CDCl$_3$ + CD$_3$OD) δ 7.7∼7.4(3H, m), 7.32(1H, d), 7.1∼6.8(2H, m), 2.15(3H, s), 1.35(9H, s) |

TABLE VII-continued

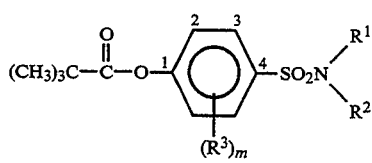

| Example No. —R³* | Name | TLC | IR (cm⁻¹) or NMR |
|---|---|---|---|
| 5(13) COOH —NH—⟨⟩ 2,6-diCH₃ | 2,6-dimethyl-4-[N-(o-carboxyphenyl) sulfamoyl]phenyl ester of pivalic acid | Rf 0.28 (ethyl acetate: hexane: acetic acid = 10:20:0.5) | ν 3500~2500, 1750, 1660, 1580, 1480, 1420, 1340, 1250, 1150, 1100 |
| 5(14) COOH —NH—⟨⟩—OCOCH₃ 2-CH₃ | 2-methyl-4-[N-(2-carboxy-4-acetyloxyphenyl)sulfamoyl]phenyl ester of pivalic acid | Rf 0.33 (chloroform: methanol: acetic acid = 100:5:1) | (CDCl₃) δ 7.8~7.1(5H, m), 7.0(1H, d), 2.3(3H, s), 2.15(3H, s), 1.35(9H, s) |
| 5(15) COOH —NH—⟨⟩—OCO(CH₂)₄CH₃ 2-CH₃ | 2-methyl-4-[N-(2-carboy-4-hexanoyloxyphenyl)sulfamoyl] phenyl ester of pivalic acid | Rf 0.33 (chloroform: methanol: acetic acid = 100:5:1) | (CDCl₃) δ 7.75~7.40(4H, m), 7.15(1H, d, d), 6.95(1H, d), 2.45(2H, t), 2.1(3H, s), 1.35(9H, s), 0.85(3H, t) |
| 5(16) COOH —NH—⟨⟩ COOH 2-CH₃ | 2-methyl-4-[N-(2,5-dicarboxyphenyl) sulfamoyl]phenyl ester of pivalic acid | Rf 0.37 (chloroform: methanol: acetic acid = 30:3:1) | ((CD₃)₂SO) δ 7.98(2H, d), 7.4~7.2(3H, m), 7.0(1H, d), 2.1(3H, s), 1.36(9H, s) |
| 5(17) COOCH₂COOH —NH—⟨⟩ 2-CH₃ | o-(3-methyl-4-pivaloyloxybenzene) sulfonylaminobenzoyloxy acetic acid | Rf 0.33 (chloroform: methanol: acetic acid = 100:5:1) | (CDCl₃) δ 8.0~6.85(7H, m), 4.75(2H, s), 2.15(3H, s), 1.35(9H, s) |

TABLE VIII $(CH_3)_3C-\overset{O}{\underset{\|}{C}}-O-\underset{(R^3)_m}{\underset{|}{\phantom{X}}}\text{Ar}-CON\overset{R^1}{\underset{R^2}{\phantom{X}}}$

| Example No. | $-N\overset{R^1}{\underset{R^2}{\phantom{X}}}$ $-R^3*$ | Name | TLC | IR (cm$^{-1}$) or NMR |
|---|---|---|---|---|
| 5(18) | —NH—(o-COOH-phenyl) ; —H | p-[N-(o-carboxyphenyl)carbamoyl]phenyl ester of pivalic acid | Rf 0.42 (ethyl acetate: hexane: acetic acid = 10:20:0.5) | ν 1740, 1680, 1660, 1600, 1590, 1540, 1480, 1440 |
| 5(19) | —N(CH$_3$)(o-COOH-phenyl) ; —H | p-[N-(methyl-N-(o-carboxyphenyl)carbamoyl]phenyl ester of pivalic acid | Rf 0.17 (ethyl acetate: hexane: acetic acid = 10:20:0.5) | ν 1750, 1720, 1590, 1470, 1440, 1380 |
| 5(20) | —N(CH$_3$)(m-COOH-phenyl) ; —H | p-[N-(methyl-N-(m-carboxyphenyl)carbamoyl]phenyl ester of pivalic acid | Rf 0.15 methylene chloride: ethyl acetate = 30:1) | ν 1750, 1720, 1640, 1600, 1580, 1480, 1440, 1370 |

Example 6 p-[(N-methyl-N-phenyl)sulfamoyl]phenyl ester of pivalic acid

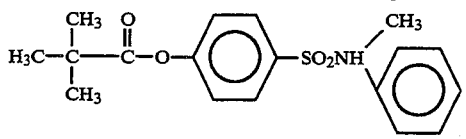

In an atmosphere of argon, THF solution (8 ml) of the compound of the present invention of Example 1 (1) (300 mg) was added to sodium hydride (37 mg) under cooling with ice, and the mixture was stirred for 2 hours.

Methyl iodide (66 μl) and hexamethylphosphoramide (HMPA) (1 ml) were added to the reaction solution, and the mixture was stirred for 30 minutes.

The reaction solution was extracted with ether, and the extract was washed with successive, water and saturated aqueous solution of sodium chloride.

And further, the solution was dried with sodium sulfate, and distilled off under reduced pressure to give the title compound (180 mg) having the following physical data.

TLC:Rf 0.61 (methylene chloride:ethyl acetate=30:1);

IR:γ 1750, 1590, 1490, 1450, 1340 cm$^{-1}$.

Hereinafter, by tile same procedure of Example 6, using corresponding derivative of pivlaic acid, the compounds of the present invention described in Table VIII were obtained.

TABLE VIII

[Structure: (CH₃)₃C—C(=O)—O—(benzene ring with positions 1,2,3,4 and R³)—CON(R¹)(R²)]

| Example No. | —N(R¹)(R²) / —R³* | Name | TLC | IR (cm⁻¹) or NMR |
|---|---|---|---|---|
| 6(1) | —N(CH₃)(p-tolyl) / —H | p-[N-methyl-N-(p-tolyl)carbamoyl] phenyl ester of pivalic acid | Rf 0.33 (methylene chloride: acetic acid = 30:1) | ν 1750, 1640, 1600, 1510, 1360, 1200 (neat) |
| 6(2) | —N(CH₃)(o-COOCH₂-phenyl-phenyl) / —H | p-[N-methyl-N-(o-benzyloxycarbonylphenyl)carbamoyl]phenyl ester of pivalic acid | Rf 0.21 (methylene chloride: acetic acid = 30:1) | ν 1750, 1720, 1640, 1600, 1370, 1250 (neat) |
| 6(3) | —N(CH₃)(m-COOCH₂-phenyl-phenyl) / —H | p-[N-methyl-N-(m-benzyloxycarbonylphenyl)carbamoyl] phenyl ester of pivalic acid | Rf 0.38 (methylene chloride: acetic acid = 30:1) | |
| 6(4) | —N(CH₃)(pyridin-3-yl) / —H | p-[N-methyl-N-(pyridine-3-yl)carbamoyl]phenyl ester of pivalic acid | Rf 0.44 (chloroform: methanol = 10:1) | ν 1750, 1650, 1480, 1420, 1380, 1200, 1110 |

Example 7

3-hydroxy-4-[(N-methyl-N-pheyl)scarbamoyl]phenyl ester of pivalic acid

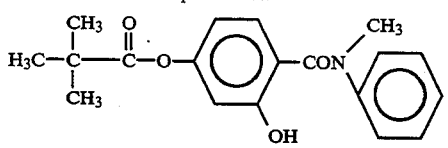

The mixture of methanol (5 ml) and triethylamine (0.3 ml) of the compound (83 mg) of the present invention obtained by procedure of Example 2 (112) was stirred for 3 hours at room temperature.

The reaction solution was extracted with ether, and the extract was washed successively with 1N-HCl, water, saturated an aqueous solution of sodium chloride.

The solution was dried with sodium sulfate, and distilled off under reduced pressure to give the title compound (68 mg) having the following physical data.

TLC:Rf 0.34 (methylene chloride:ethyl acetate=30:1);

NMR (CDCl3):δ 7.0~7.4(6H, m), 6.65(1H,d), 6.1(1H,2d), 3.5(3H,s), 1.3(9H,s).

EXAMPLES OF PREPARATIONS

The following components were admixed in conventional method and punched out to obtain 100 tablets each containing 50 mg of active ingredient.

| | |
|---|---|
| N-[o-(p-pivaloyloxybenzene)sulfonylaminobenzoyl]glycine | 5 g |
| Cellulose calcium glycolate (disintegrating agent) | 0.2 g |
| Magnesium stearate (lubricating agent) | 0.1 g |
| Microcrystaline cellulose | 4.7 g |

What is claimed is:
1. A compound of the formula:

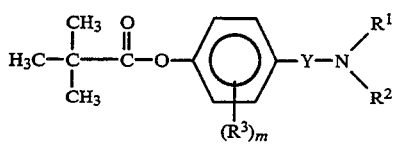 (I)

wherein Y represents sulfonyl (—SO$_2$—) or

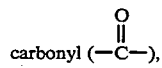
carbonyl (—C—), (i) R$^1$ and R$^2$, which may be the same or different, each represent
(1) hydrogen,
(2) an alkyl of up to 16 carbon atoms or an alkyl of up to 16 carbon atoms substituted by carboxy,
(3) a group of the formula:

wherein
X represents a single-bond, sulfonyl (—SO$_2$—), an alkylene of up to 4 carbon atoms, or an alkylene of up to 4 carbon atoms substituted by —COOH or benzyloxy-carbonyl

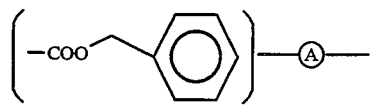

represents a carbocyclic ring or a heterocyclic ring, n represents an integer of 1 to 5,
R$^4$ which may be the same or different represents,
(1) hydrogen or an alkyl group of up to 8 carbon atoms,
(2) an alkoxy of up to 14 carbon atoms,
(3) an alkylthio of up to 6 carbon atoms,
(4) hydroxy, halogen, nitro or trihalomethyl,
(5) a group of the formula: —NR$^{41}$R$^{42}$ wherein R$^{41}$ and R$^{42}$, which may be the same or different, each represents hydrogen or alkyl of up to 4 carbon atoms,
(6) tetrazole,
(7) sulfonic acid (—SO$_3$H) or hydroxymethyl (—CH$_2$OH),
(8) a group of the formula: —SO$_2$NR$^{41}$R$^{42}$ wherein R$^{41}$ and R$^{42}$ have the same meanings as described hereinbefore,
(9) a group of the formula: —Z$^{41}$—COOR$^{43}$ wherein Z$^{41}$ represents a single-bond, an alkylene of up to 4 carbon atoms, or an alkenylene of from 2 to 4 carbon atoms, R$^{43}$ represents hydrogen, an alkyl of up to 4 carbon atoms or benzyl,
(10) a group of the formula: —CONR$^{41}$R$^{42}$ wherein R$^{41}$ and R$^{42}$ have the same meanings as described hereinbefore,
(11) a group of the formula: —COO—Z$^{42}$—COOR$^{43}$ wherein Z$^{42}$ represents an alkylene of up to 4 carbon atoms, R$^{43}$ represents hydrogen or an alkyl of up to 4 carbon atoms,
(12) a group of the formula: —COO—Z$^{42}$—CONR$^{41}$R$^{42}$ wherein Z$^{42}$, R$^{41}$ and R$^{42}$ have the same meanings as described hereinbefore,
(13) a group of the formula: —OCO—R$^{45}$ wherein R$^{45}$ represents an alkyl of up to 8 carbon atoms or p-guanidinophenyl,
(14) a group of the formula: —CO—R$^{46}$ wherein R$^{46}$ represents an alkyl of up to 4 carbon atoms,
(15) a group of the formula: —O—Z$^{43}$—COOR$^{45}$ wherein Z$^{43}$ represents an alkylene of up to 6 carbon atoms, R$^{45}$ represents a hydrogen atom, an alkyl group of up to 8 carbon atoms or a p-guanidinophenyl group,
(16) a group of the formula:

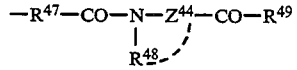

wherein —N—Z$^{44}$—CO represents an amino acid residue, R$^{48}$ represents hydrogen or alkyl of up to 4 carbon atoms, and R$^{49}$ represents hydroxy, alkoxy of up to 4 carbon atoms, amino unsubstituted or substituted by one or two alkyls of up to 4 carbon atoms, carbamoylmethoxy unsubstituted or substituted by one or two alkyls of up to 4 carbon atoms at nitrogen of carbamoyl, R$^{47}$ represents a single-bond or an alkyl of up to 4 carbon atoms, or wherein

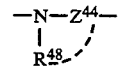

represents a heterocyclic ring containing 3 to 6 carbon atoms and R$^{47}$ and R$^{49}$ each has the same meaning as described hereinbefore,
(ii) R$^1$, R$^2$ and nitrogen bonded to R$^1$ and R$^2$ together represent a heterocyclic ring containing at least one nitrogen and substituted by —COOH, or an unsubstituted heterocyclic ring containing at least one nitrogen, R$^3$ represents
(1) hydrogen,
(2) hydroxy,
(3) an alkyl of up to 6 carbon atoms,
(4) halogen,
(5) an alkoxy of up to 4 carbon atoms,
(6) an acyloxy of 2 to 5 carbon atoms, m represents an integer of up to 4, with the proviso that (1) when R$^1$ and R$^2$ represent hydrogen atom or alkyl group of up to 16 carbon atoms, and R$^3$ represents a hydrogen atom or an alkyl group of up to 6 carbon atoms, Y represents carbonyl (—CO—),
and that (2) the compounds wherein one of R$^1$ and R$^2$ represents hydrogen or an alkyl group of up to 16 carbon atoms or 2-carboxyethyl and the other of R$^1$ and R$^2$ represents a group of the formula:

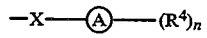

wherein X has the same meaning as described hereinbefore,

represents a pyridine or pyrrole ring, n represents an integer of 1 or 2, $R^4$ which may be the same or different represents a hydrogen, an alkyl group of up to 8 carbon atoms or a group of the formula: $-Z^{41}-COOR^{43}$ wherein $Z^{41}$ and $R^{43}$ have the same meaning as described hereinbefore, m represents an integer of 1 or 2 and Y and $R^3$ have the same meaning as described hereinbefore, are excluded, or pharmaceutically acceptable salts thereof.

2. A compound according to claim 1, wherein Y is sulfonyl ($-SO_2-$).

3. A compound according to claim 1, wherein

—(A)— is a carbocyclic ring.

4. A compound according to claim 1, wherein

—(A)— is phenyl.

5. A compound according to claim 1, wherein one of $R^4$ is an amino acid-residue.

6. A compound according to claim 1, wherein an amino acid-residue of $R^4$ is a glycine-residue.

7. A compound according to claim 1, wherein an amino acid-residue of $R^4$ is alanine-residue.

8. A compound according to claim 6, which is selected from the group consisting of:
N-[o-(p-pivaloyloxybenzene)sulfonylaminobenzoyl]glycine,
N-[2-(p-pivaloyloxybenzene)sulfonylamino-5-chlorobenzoyl]glycine,
N-[5-methylthio-2-(p-pivaloyloxybenzene)sulfonylaminobenzoyl]glycine,
N-[2-(p-pivaloyloxybenzene)sulfonylamino-5-propylthiobenzoyl]glycine,
N-[5-methyl-2-(p-pivaloyloxybenzene)sulfonylaminobenzoyl]glycine, and
N-[o-(p-pivaloyloxybenzene)sulfonylaminobenzoyl]glycine methylester.

9. A compound according to claim 7, which is selected from the group consisting of:
N-[o-(3-methyl-4-pivaloyloxybenzene)sulfonylaminobenzoyl]-d 1-alanine,
N-[o-(3-methyl-4-pivaloyloxybenzene)sulfonylaminobenzoyl]-β-alanine,
N-[o-(e-methyl-4-pivaloyloxybenzene)sulfonylaminobenzoyl]-1-alanine,
N-[5-chloro-2-(3-methyl-4-pivaloyloxybenzene)sulfonylaminobenzoyl]-1-alanine and
N-[5-chloro-2-(3-methyl-4-pivaloyloxybenzene)sulfonylamino-benzoyl]-β-alanine.

10. A pharmaceutical composition for the treatment of pulmonary emphysema, atherosclerosis and rheumatoid arthritis, which comprises, as active ingredient, an effective amount of at least one compound of the formula (I) depicted in claim 1, wherein various symbols are as defined in claim 1, together with a pharmaceutically acceptable carrier.

11. A method for the treatment of pulmonary emphysema, atherosclerosis and rheumatoid arthritis comprising administering to a patient in need of same, a pharmaceutical composition which comprises, as active ingredient, an effective amount of at least one compound of the formula (I) of claim 1.

* * * * *